(12) United States Patent
Fouts et al.

(10) Patent No.: US 8,870,749 B2
(45) Date of Patent: Oct. 28, 2014

(54) ARRANGEMENT FOR MINIMAL ACCESS SURGERY

(75) Inventors: Brian Fouts, San Martin, CA (US);
Daniel E. Cooper, Dallas, TX (US);
Reid Cover, Mountain View, CA (US);
Michael Baycura, San Francisco, CA (US)

(73) Assignee: Stryker Corporation, Kalamazoo, MI (US)

( * ) Notice: Subject to any disclaimer, the term of this patent is extended or adjusted under 35 U.S.C. 154(b) by 189 days.

(21) Appl. No.: 13/600,889

(22) Filed: Aug. 31, 2012

(65) Prior Publication Data
US 2013/0060084 A1    Mar. 7, 2013

Related U.S. Application Data

(60) Provisional application No. 61/573,280, filed on Sep. 2, 2011.

(51) Int. Cl.
*A61B 1/00* (2006.01)
*A61B 17/34* (2006.01)

(52) U.S. Cl.
CPC ......... *A61B 17/3421* (2013.01); *A61B 17/3462* (2013.01); *A61B 2017/3445* (2013.01); *A61B 2017/3447* (2013.01); *A61B 2017/347* (2013.01); *A61B 2017/3492* (2013.01)
USPC ............................... 600/114; 600/106; 606/1

(58) Field of Classification Search
CPC ........... A61B 17/3421; A61B 17/3462; A61B 2017/3445; A61B 2017/3447; A61B 2017/347; A61B 2017/3492; A61B 1/00137; A61B 1/00135; A61B 1/00154; A61B 1/01; A61B 1/012; A61B 1/0125; A61B 1/015; A61B 1/018; A61M 39/0613; A61M 39/00
USPC .............. 600/102, 106, 208, 114; 606/1
See application file for complete search history.

(56) References Cited

U.S. PATENT DOCUMENTS

| | | | |
|---|---|---|---|
| 5,171,245 A | 12/1992 | Cezana | |
| 5,395,317 A | 3/1995 | Kambin | |
| 5,456,673 A * | 10/1995 | Ziegler et al. | 604/264 |
| 5,762,629 A | 6/1998 | Kambin | |
| 5,897,087 A * | 4/1999 | Farley | 248/229.21 |
| 6,454,783 B1 | 9/2002 | Piskun | |

(Continued)

OTHER PUBLICATIONS

Covidien—P-navel systems: pictures and description published on the internet before Sep. 2, 2010 (2 pages).

(Continued)

*Primary Examiner* — John P Leubecker
*Assistant Examiner* — Arnaldo Torres Diaz
(74) *Attorney, Agent, or Firm* — Flynn, Thiel, Boutell & Tanis, P.C.

(57) ABSTRACT

An access and positioning arrangement for use during an endoscopic surgical procedure in which a pair of surgical tools are utilized, such as an endoscopic imaging device for providing an image of the surgical site and a surgical instrument for manipulating tissue at the surgical site. The arrangement includes a housing for positioning over a surgical portal defined in the patient through which the surgical site is accessed, which housing defines first and second channels which receive the respective surgical tools so that the tools can be maintained in a fixed orientation relative to one another within the surgical site and so that the tools can be readily positioned in the correct positions relative to one another at the surgical site.

25 Claims, 17 Drawing Sheets

(56) References Cited

U.S. PATENT DOCUMENTS

| | | | |
|---|---|---|---|
| 6,652,488 B1* | 11/2003 | Keast et al. | 604/118 |
| 6,808,505 B2 | 10/2004 | Kadan | |
| 6,945,983 B2* | 9/2005 | Dittrich et al. | 606/185 |
| 7,066,879 B2 | 6/2006 | Fowler et al. | |
| 7,249,602 B1 | 7/2007 | Emanuel | |
| 7,344,547 B2 | 3/2008 | Piskun | |
| 7,562,855 B2* | 7/2009 | Oetlinger | 248/316.6 |
| 8,061,359 B2 | 11/2011 | Emanuel | |
| 8,096,941 B2 | 1/2012 | Fowler et al. | |
| 2004/0158203 A1* | 8/2004 | Cover et al. | 604/118 |
| 2004/0176763 A1* | 9/2004 | Foley et al. | 606/60 |
| 2004/0186346 A1* | 9/2004 | Smith et al. | 600/102 |
| 2005/0043690 A1* | 2/2005 | Todd | 604/248 |
| 2007/0032700 A1 | 2/2007 | Fowler et al. | |
| 2007/0032701 A1 | 2/2007 | Fowler et al. | |
| 2007/0282266 A1 | 12/2007 | Davidson | |
| 2008/0027476 A1 | 1/2008 | Piskun | |
| 2008/0058588 A1 | 3/2008 | Emanuel | |
| 2008/0058842 A1 | 3/2008 | Emanuel | |
| 2008/0161826 A1* | 7/2008 | Guiraudon | 606/108 |
| 2009/0012530 A1 | 1/2009 | Fowler | |
| 2009/0093682 A1* | 4/2009 | Izzo et al. | 600/201 |
| 2009/0259200 A1* | 10/2009 | Lampropoulos et al. | 604/249 |
| 2010/0081875 A1 | 4/2010 | Fowler et al. | |
| 2010/0100112 A1* | 4/2010 | Kauker et al. | 606/180 |
| 2010/0130824 A1 | 5/2010 | Piskun | |
| 2010/0130825 A1 | 5/2010 | Piskun | |
| 2010/0130826 A1 | 5/2010 | Piskun | |
| 2010/0137691 A1 | 6/2010 | Piskun | |
| 2011/0060183 A1* | 3/2011 | Castro et al. | 600/104 |
| 2011/0230723 A1* | 9/2011 | Castro et al. | 600/205 |
| 2011/0301578 A1* | 12/2011 | Muniz-Medina et al. | 606/1 |
| 2012/0004502 A1* | 1/2012 | Weitzner et al. | 600/102 |
| 2012/0035416 A1* | 2/2012 | Fernandez et al. | 600/102 |
| 2012/0116362 A1* | 5/2012 | Kieturakis | 606/1 |
| 2012/0158015 A1 | 6/2012 | Fowler et al. | |
| 2013/0103057 A1* | 4/2013 | Keating et al. | 606/146 |

OTHER PUBLICATIONS

Covidien—SILS Port: pictures and description published on the internet before Sep. 2, 2010 (2 pages).

Advanced Surgical Devices—TriPort and QuadPort devices: pictures and description published on the internet before Sep. 2, 2010 (1 page).

Endo Ethicon—Single Site Laparoscopy Device: pictures and description published on the internet before Sep. 2, 2010 (1 page).

* cited by examiner

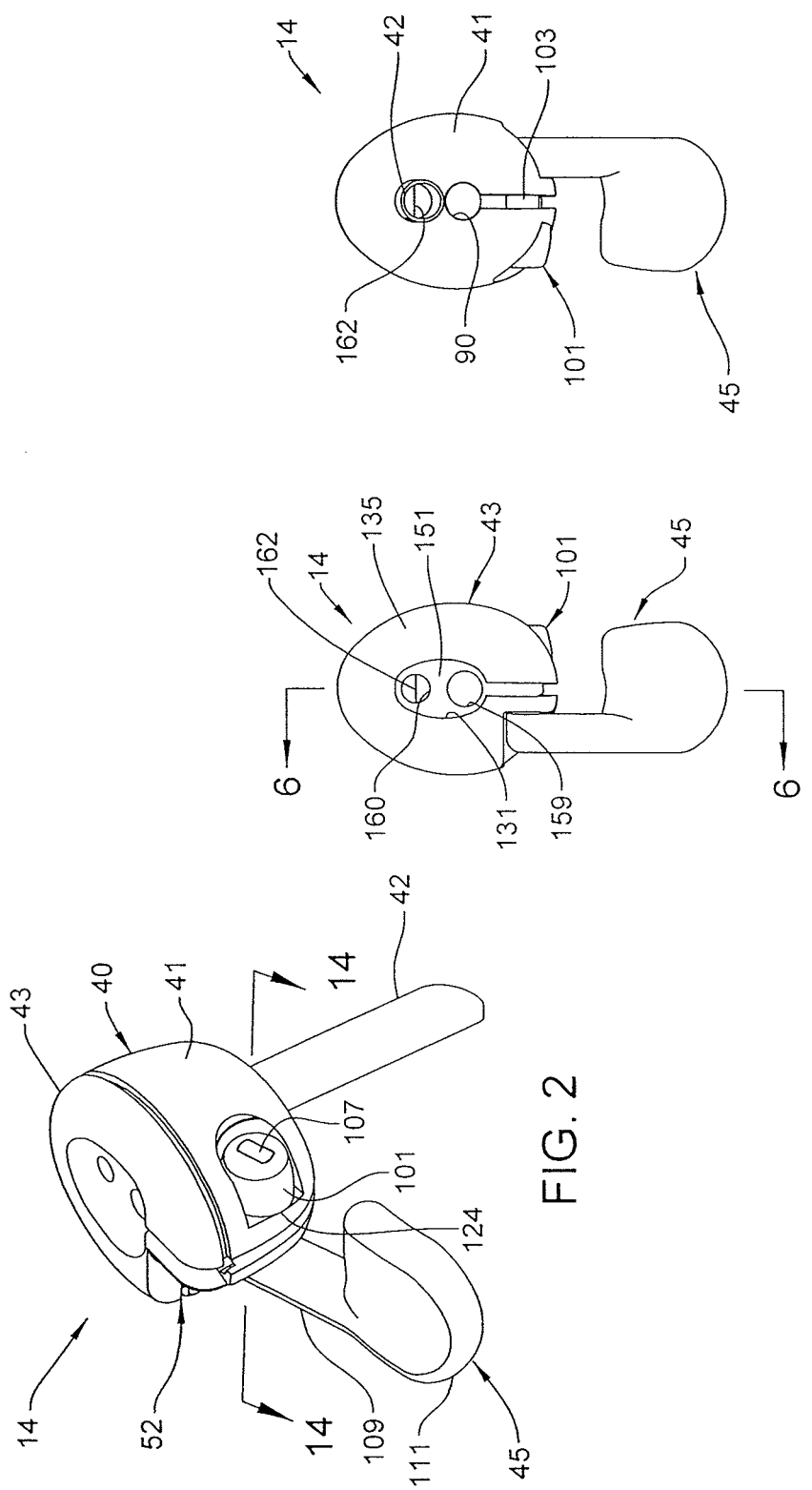

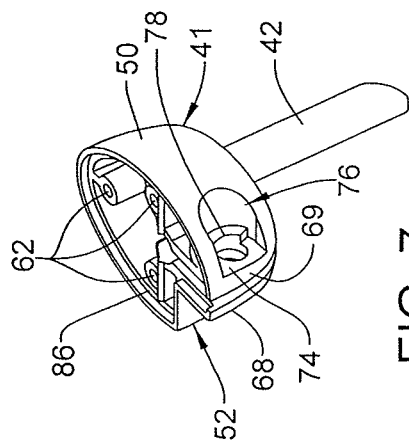
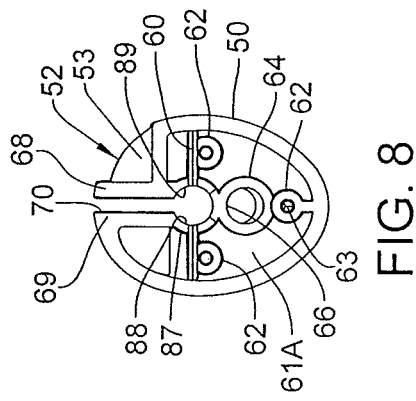
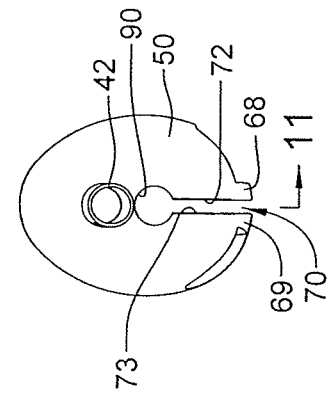
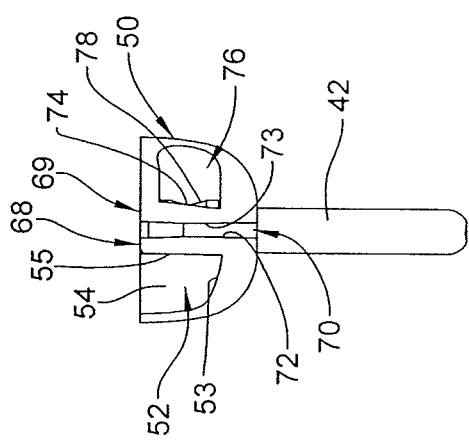
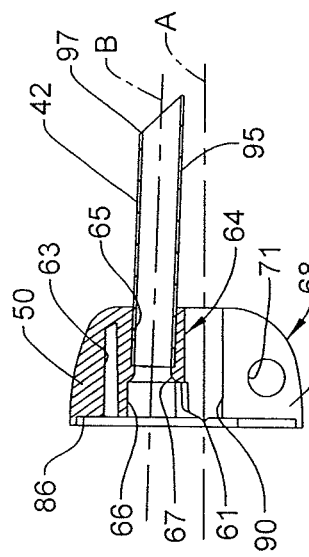
FIG. 7
FIG. 8
FIG. 9
FIG. 10
FIG. 11

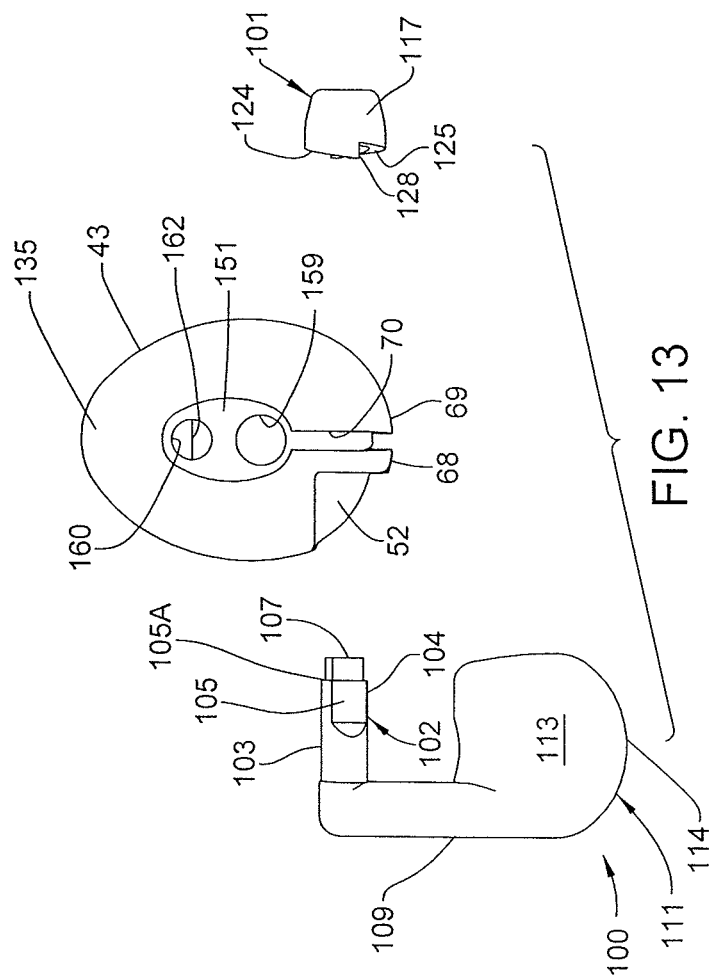
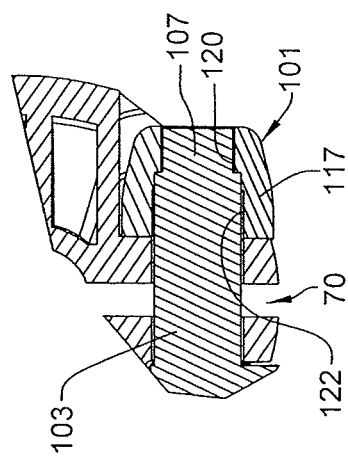

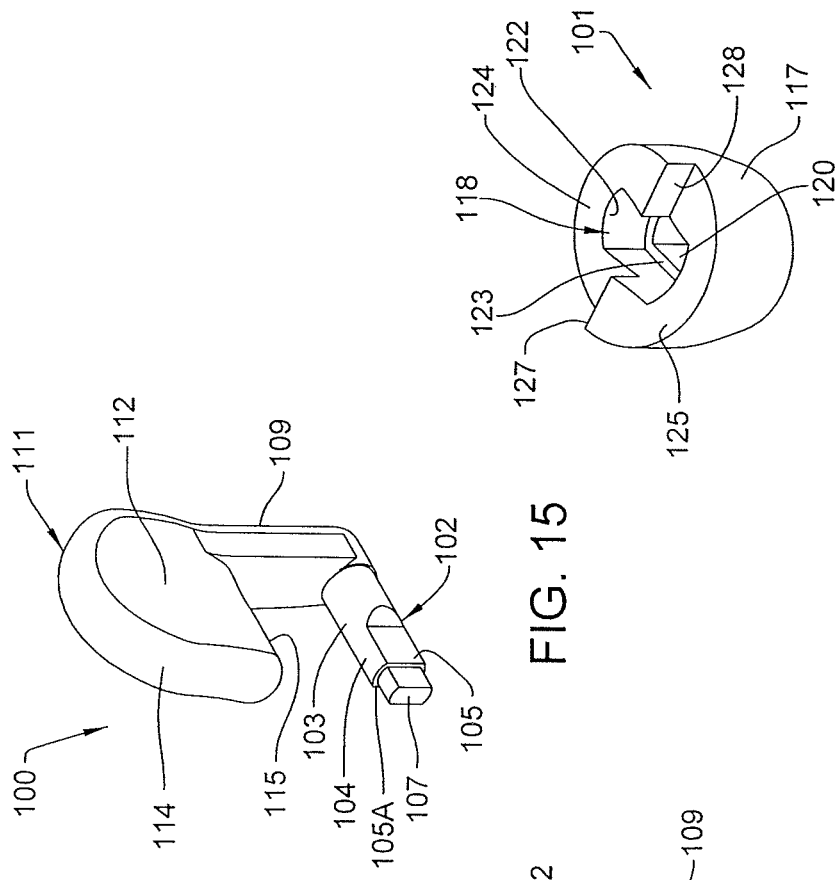
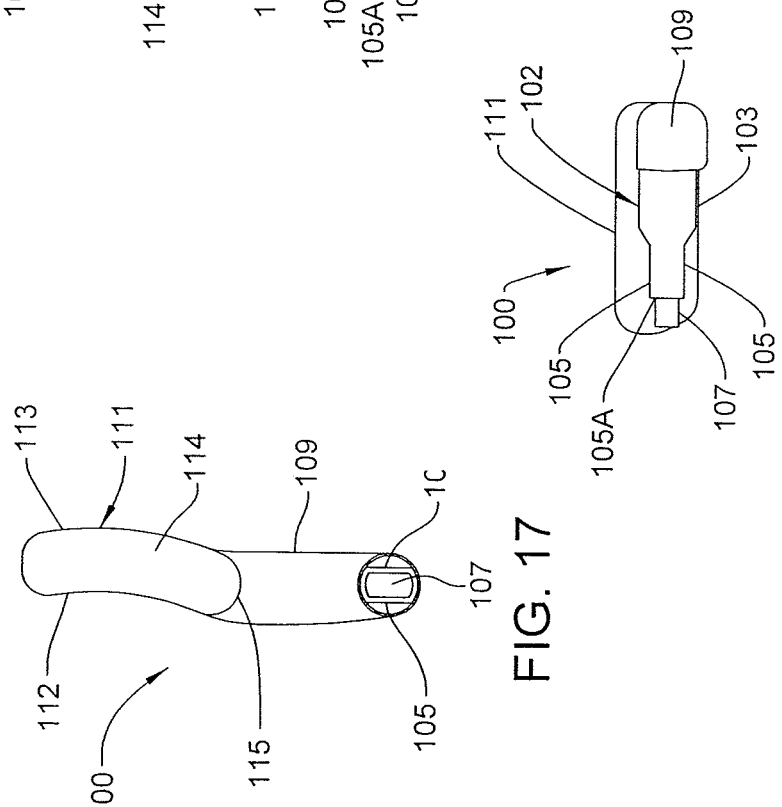
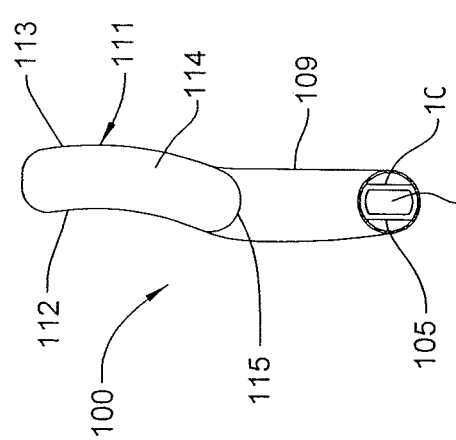

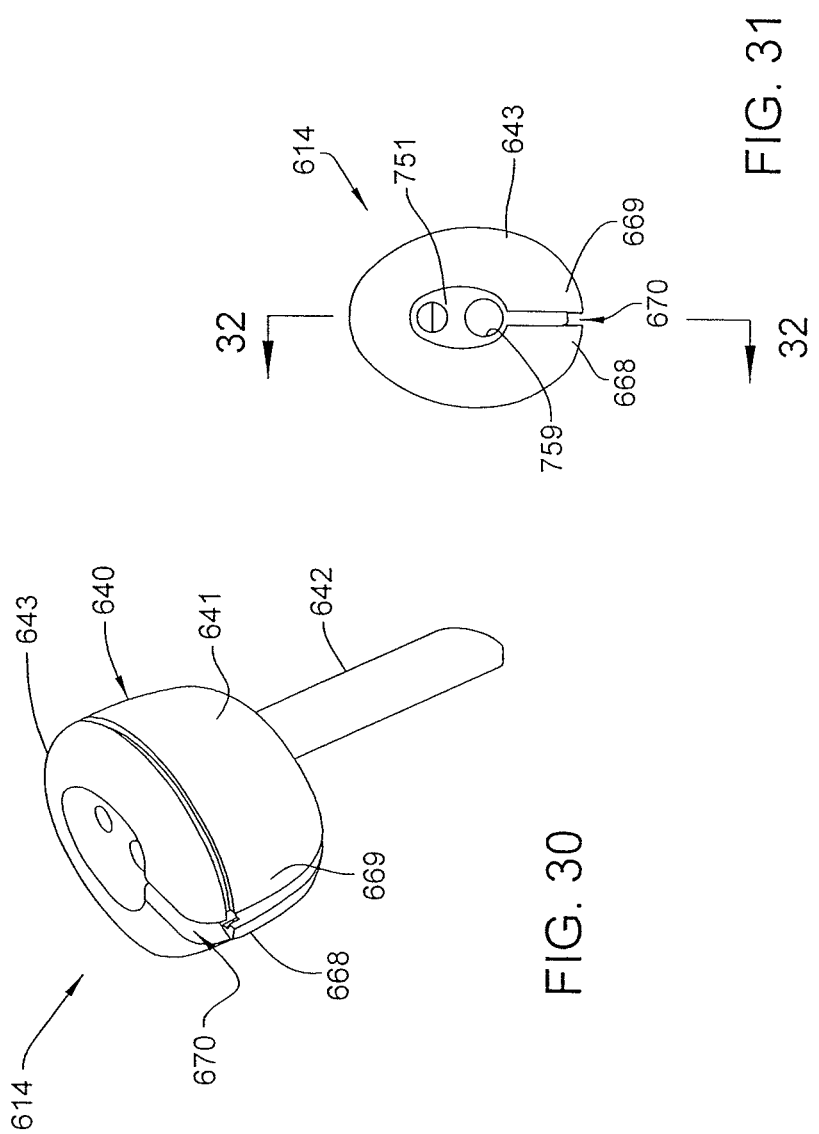

ARRANGEMENT FOR MINIMAL ACCESS SURGERY

CROSS REFERENCE TO RELATED APPLICATION

This claims the benefit of U.S. Provisional Application No. 61/573,280, filed Sep. 2, 2011, the disclosure of which is hereby incorporated by reference in its entirety.

FIELD OF THE INVENTION

The present invention relates to an arrangement for performing endoscopic minimal access surgery in conjunction with multiple surgical instruments, one of which may include an imaging apparatus, such as an endoscope.

BACKGROUND OF THE INVENTION

Endoscopy is a minimally invasive surgical procedure which utilizes imaging apparatus for the purpose of providing a view of an interior portion of the body, without requiring that a large surgical opening be made in the patient to gain access to the surgical site. An endoscope is one type of such imaging apparatus which is placed in the body at the location at which it is necessary to perform a surgical procedure. Along with the endoscope, other types of surgical tools or instruments may be placed in the body at the surgical site so as to carry out a particular procedure. Examples of such instruments are cutting instruments, such as shaver-type devices which mechanically cut bone and hard tissue, or radio-frequency (RF) probes which are used to remove tissue via ablation or to coagulate tissue to minimize bleeding at the surgical site, to name only a few. In an endoscopic procedure, the surgeon views the surgical site through the endoscope in order to manipulate the other surgical instrument or instruments so as to perform the desired surgical procedure.

The development of endoscopes and their companion surgical instruments has made it possible to perform minimally invasive surgery that requires only small openings to be made in the patient, which openings are called portals. One advantage of performing endoscopic surgery is the reduction of the number of incisions made in the patient and/or the reduction of incision size, which reduces healing time after surgery. Still another advantage of endoscopic surgery is that it exposes less of the interior tissue of the patient's body to the open environment. This minimal opening of the patient's body lessens the extent to which the internal tissue and organs are open to infection.

In traditional endoscopic surgery, the endoscope and the surgical instrument are introduced to the surgical site through separate small portals, and once inside the patient, the instrument and endoscope must be correctly spatially oriented relative to one another through triangulation. Specifically, the surgeon must place the working end, typically the distal end, of the surgical instrument within the field of view of the endoscope so that the surgical instrument can be correctly manipulated, and must continually maintain this correct spatial relationship between the endoscope and the instrument throughout the surgical procedure. Since the surgical instrument and endoscope are inserted into the patient at varying angles and from separate locations, maintaining the correct spatial relationship between the two devices can be taxing on the surgeon. Further, during multiple-portal endoscopic surgery, surgical instruments, such as the blade of a surgical shaver or an RF probe, may collide with the endoscope optics, which can damage the endoscope and/or potentially cause a delay in surgery. Additionally, it can be difficult for surgeons to maintain the proper location of the endoscope within the surgical site during surgery.

While endoscopic surgery has been very successful in carrying out various surgical procedures, the medical field continually strives to lessen trauma caused to the patient during an endoscopic surgical procedure, and the number of portals created in the patient has been reduced from three portals to two portals by expanding the functionality of the endoscope itself and of other surgical instruments. Further, the present trend in endoscopic procedures is to perform all necessary surgical functions through a single portal. One of the challenges presented by single-port surgical procedures is preventing stretching and/or tearing of the incision defining the single portal as the surgical instruments are manipulated and levered relative to the patient while same extend into the patient through the portal.

In view of the above, one object of the present invention is to require the formation of only a small, single incision in the patient during endoscopic surgery by maintaining the various surgical instruments and the endoscope in the correct spatial orientation relative to one another to effectively prevent undesirable deviation of these tools during surgery, and to maintain the endoscope at the proper depth within the surgical site. A further object is to allow ready positioning of the surgical instrument relative to the endoscope so that the surgical instrument is inserted into the patient directly into the field of view of the endoscope.

In this regard, the present invention includes an access and positioning arrangement which is intended for placement or positioning adjacent or in some situations atop the skin of the patient where the incision or portal is located and through which portal the surgical site is accessed. The arrangement according to the invention thus acts an exterior access point to the surgical site which effectively defines multiple pathways leading thereto through a single incision defined within the patient. The arrangement includes a hub having a housing defining therein a pair of channels which are sidewardly-spaced from one another within an interior of the housing and which communicate with the surgical site via the portal defined in the patient. Respective surgical instruments or tools are inserted into the respective channels for extension into the surgical site through the portal, which channels serve to maintain the instruments in a predefined and fixedly-spaced relation with one another.

The arrangement in some embodiments additionally includes a clamping or locking arrangement which cooperates with at least one of the channels defined in the housing so as to non-movably fix the surgical instrument located within the channel relative to the housing and/or at the proper location within and relative to the surgical site. According to a preferred usage of the arrangement, one of the surgical instruments is an endoscope assembly including an elongated shaft which is inserted in the aforementioned channel or scope channel, and when located at the proper depth or location relative to the housing and/or surgical site, the clamping arrangement is engaged so as to fix the endoscope assembly at the selected position. A further surgical instrument, such as a shaver, burr or drill, for example, is inserted into the opposite or working channel defined in the housing and can be utilized to manipulate tissue at the surgical site. In this regard, the working or distal end of the shaver or other instrument must be placed and maintained within the field of view of the endoscope so that the surgeon can correctly manipulate the instrument and carry out the surgical procedure. In this regard, one embodiment of the invention incorporates an elongate channel member which is cantilevered from the housing in a position so as to communicate with, and form an extension of, the working channel through which the shaver or other tissue-manipulating instrument extends. The length of the channel member as well as the orientation of same relative to the scope channel defined in the housing is such that the tissue-manipulating instrument can be readily placed and maintained in the field of view of the endoscope during the surgical procedure.

The arrangement according to one embodiment of the invention incorporates a sealing arrangement so as to prevent undesirable fluid leakage from the surgical site and also to help maintain in-joint pressure when the arrangement is utilized in arthroscopic surgery, for example. In a further embodiment, the seal arrangement and channel member are dispensed with which provides more flexibility in positioning the surgical instrument by allowing the surgeon to achieve a greater angle of deviation between the surgical instrument and the endoscope.

As an alternative to a clamping or locking arrangement which is actively engaged or disengaged by the user, the surgical instrument can be fixed in a desired position relative to the housing utilizing a friction-fit or interference-type arrangement. In this regard, at least one of the channels defined in the housing engages the surgical instrument inserted therein with a friction or interference-type fit such that the instrument can be maintained at the desired depth relative to the surgical site and/or relative to the housing simply by inserting the instrument into the channel until the desired depth is reached.

BRIEF DESCRIPTION OF THE DRAWINGS

FIG. 2 is a top and front perspective view of the access and positioning arrangement according to the first embodiment of the invention;

FIG. 3 is a top view of the access and positioning arrangement of FIG. 2;

FIG. 4 is bottom view of the access and positioning arrangement of FIG. 2;

FIG. 7 is a top and front perspective view of the hub assembly of the access and positioning arrangement of FIG. 2, without the top cover, seal arrangement and locking arrangement;

FIG. 8 is a top view of the hub assembly of FIG. 7;

FIG. 9 is a bottom view of the hub assembly of FIG. 7;

FIG. 10 is front view of the hub assembly of FIG. 7;

FIG. 11 is a cross-sectional view of the hub assembly as seen generally along line 11-11 in FIG. 9;

FIG. 13 is an exploded top view of the hub assembly of FIG. 2;

FIG. 14 is an enlarged cross-sectional view of the hub assembly as seen generally along line 14-14 in FIG. 2;

FIG. 15 is an enlarged perspective view of the actuator arm of the locking arrangement of the hub assembly;

FIG. 16 is an end view of the arm of FIG. 15;

FIG. 17 is a side view of the arm of FIG. 15;

FIG. 18 is a top perspective view of the cap of the locking arrangement;

FIG. 30 is a top and front perspective view of a third embodiment of the access and positioning arrangement according to the invention;

FIG. 31 is a top view of the access and positioning arrangement of FIG. 30;

Figure 1:
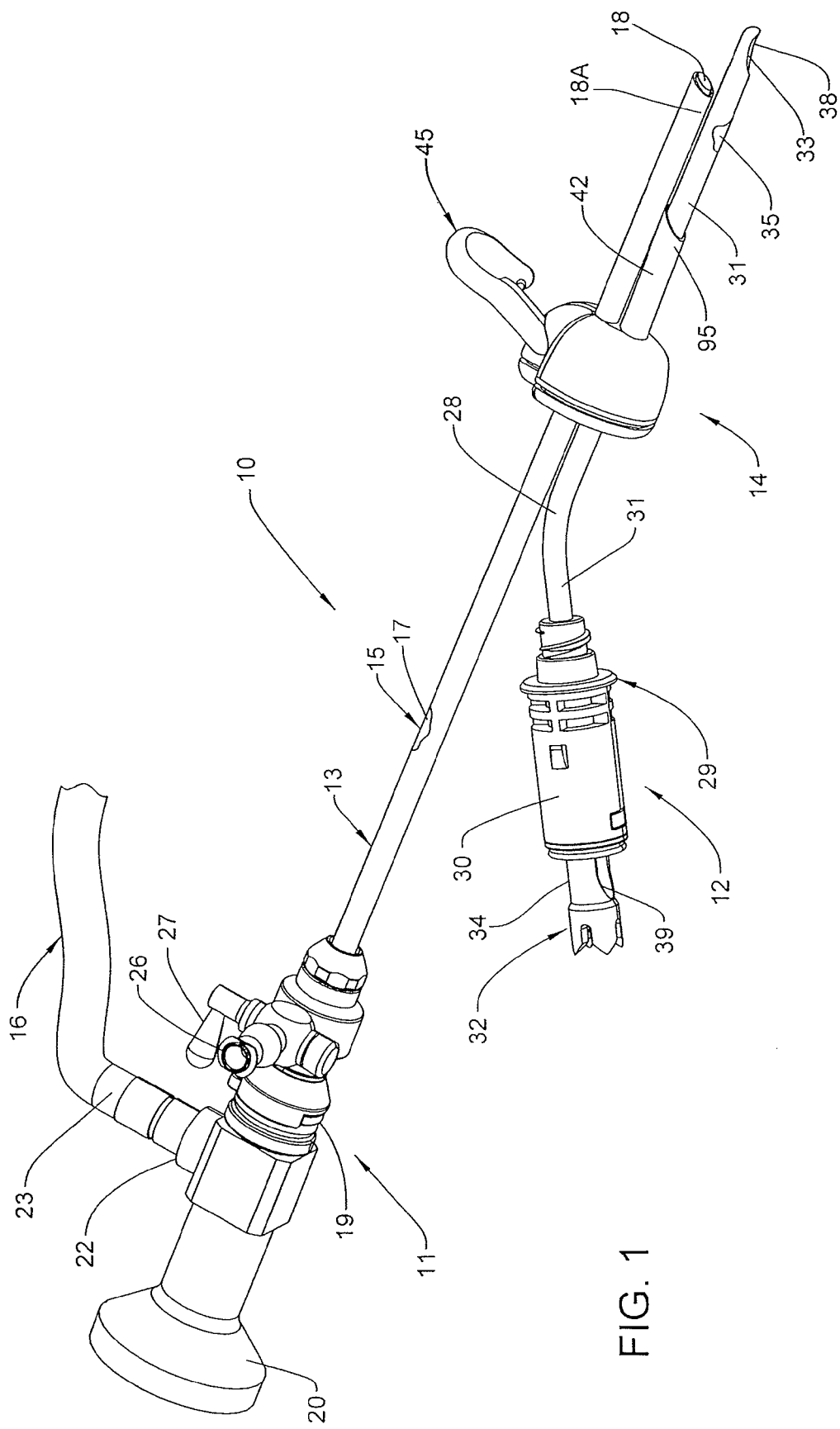
FIG. 1 is an illustration of a surgical tool arrangement for use in an endoscopic surgical procedure which incorporates the access and positioning arrangement according to a first embodiment of the invention, and illustrating examples of two types of surgical instruments usable therewith.

Certain terminology will be used in the following description for convenience in reference only, and will not be limiting. For example, the words "upwardly", "downwardly", "rightwardly" and "leftwardly" will refer to directions in the drawings to which reference is made. The words "inwardly" and "outwardly" will refer to directions toward and away from, respectively, the geometric center of the arrangement and designated parts thereof. The words "forwardly" and "distally" will refer to the direction toward the end of the arrangement which is closest to the patient, and the words "rearwardly" and "proximally" will refer to the direction toward the end of the arrangement which is furthest from the patient. Said terminology will include the words specifically mentioned, derivatives thereof, and words of similar import.

DETAILED DESCRIPTION

FIG. 1 illustrates a surgical tool arrangement 10 for carrying out a surgical procedure, such as an endoscopic procedure. One specific endoscopic procedure in which arrangement 10 may be utilized is an arthroscopic procedure wherein examination and/or treatment of damage of the interior of a joint, such as the knee, wrist, or shoulder, is carried out. The tool arrangement 10 according to the invention may be used to carry out an endoscopic procedure utilizing a limited number of incisions, and preferably a single incision or port defined in the patient. The surgical tool arrangement 10 generally includes an endoscope assembly 11, a surgical instrument 12, and an access and positioning arrangement 14. As discussed in further detail below, the endoscope assembly 11 and surgical instrument 12 are assembled to the access and positioning arrangement 14 for the purpose of carrying out an endoscopic procedure.

The endoscope assembly 11 is conventional and will accordingly only be briefly described herein. Endoscope assembly 11 includes an outer cannula 13 which houses therein an endoscope 15, a transmission cable 16 and a console or light source (not shown). Endoscope 15 is defined by an elongated and generally hollow shaft 17 with a distal end 18 configured for insertion within a body cavity and located adjacent and within a distal end 18A of cannula 13. Cannula 13 has a proximal end 19 which mounts thereon an eyepiece 20 configured to provide a viewing port through which the surgeon views the surgical field, for example, through connection between the viewing port, a digital camera, and a display screen or monitor. A light port 22 is connected to the light source to selectively transmit light to a target at the surgical site via endoscope 15.

Transmission cable 16 is configured to transmit light from a proximal end (not shown) of cable 16 associated with the light source to a distal end 23 of cable 16 attached to light port 22. In one embodiment, transmission cable 16 incorporates optical fibers suited to transmit electromagnetic radiation via total internal reflection of such radiation within the fiber material. Proximal end and distal end 23 of cable 16 include geometries, such as plugs, conducive to receiving and emitting, respectively, electromagnetic radiation.

The light source selectively provides electromagnetic radiation, such as visible light, for use in the operating theater. In one embodiment, the candlepower of light emitted from the light source is selectively adjustable via a switch. Further, light source includes a socket to which intermediary devices, such as cable 16, are connected to transmit light from light source to instruments such as endoscope 15.

Endoscope 15 contains a number of internal mechanisms which are not shown here, one of which is an imaging arrangement in the form of an optical train having one or more lenses which transmit an image from distal end 18 to eyepiece 20. Shaft 17 of endoscope 15 incorporates mounting structures which maintain alignment of the components of the optical train toward eyepiece 20, whereby electromagnetic radiation from the light source may be transmitted into endoscope 15 via cable 16 and light port 22. Further, cannula 13 in the illustrated embodiment mounts thereon a fluid port 26 which communicates with a fluid source or pump (not shown) to allow delivery of fluid to the surgical site, such as into a joint to distend same during arthroscopic surgery. Fluid port 26 is opened and closed via a valve 27. The fluid entering fluid port 26 is delivered to the surgical site through cannula 13 and exits cannula 13 at the distal end 18A thereof.

It will be appreciated that endoscope 15 may include, instead of an imaging arrangement embodied by an optical train as mentioned above, a compact imaging device such as a charged-coupled device (CCD) or a metal-oxide-semiconductor (CMOS) arranged at the distal end 18 of endoscope 15, which is configured to process and/or transmit information received from a lens or a lens assembly located distally therefrom. Instead of directing the otherwise unprocessed light information via an optical train, such information is communicated as a processed signal to a console via a wired connection.

It will also be appreciated that cannula 13 may alternatively include multiple fluid ports, instead of just fluid port 26. Specifically, cannula 13 may include a fluid inflow port and a fluid outflow port, as well as a suitable valve arrangement to allow control of such ports. Such an arrangement is conventional and allows the surgeon to both deliver fluid to the surgical site as well as remove fluid from the surgical site via the cannula 13, to thereby maintain a desirable fluid pressure at the surgical site.

Turning now to surgical instrument 12, such instrument may be in the form of a cutting instrument, such as a shaver-type device which mechanically cuts bone and hard tissue, a radio-frequency (RF) probe, or other type of tissue-manipulating tool. For purposes of illustration, the surgical instrument 12 is a conventional cutter or shaver, and thus will not be described in detail herein. The instrument 12 generally includes an outer housing assembly 29 including a hub 30 and an elongated outer tube 31 fixed to and projecting outwardly from hub 30. In the illustrated embodiment, outer tube 31 includes a bend 28 at its proximal end, and a distal end which defines a cutting window 33 therein. Instrument 12 additionally includes a cutting element 32 located within outer housing assembly 29. Cutting element 32 includes a hub 34 which is configured for engaging with a drive element of a surgical handpiece (not shown here), and an inner cutting tube or drive shaft 35 which is fixed to and projects from hub 34 and extends within outer tube 31. Distal end of cutting tube 35 cooperates with cutting window 33 of outer tube 31.

Specifically, in the illustrated embodiment, the distal end of cutting tube 35 defines therein a cutting window 38 which, upon rotation of cutting element 32 relative to and within outer housing assembly 29, effectively cuts or shaves tissue in cooperation with window 33 of outer tube 31. Further, inner tube 35 defines therein a suction passage which is in communication with a suction port 39 defined in hub 34. Suction port 39 communicates with a suction arrangement located within the handpiece so that suction can be applied to the surgical site via instrument 12.

Turning now to access and positioning arrangement 14, and with reference to FIGS. 2-6 and 10, arrangement 14 includes a hub assembly 40, which hub assembly 40 includes a generally hollow hub 41, a tubular channel or working channel member 42 which is fixed to and projects downwardly from a lower side or bottom of hub 41, a lid or cover 43 which closes off an upper open end of hub 41, and a locking or clamping arrangement 45.

Hub 41 is defined by a wall structure, which in one embodiment may be formed by molding, which wall structure includes a rounded, generally bowl-shaped and upwardly-opening outer housing wall 50. Housing wall 50 includes a recess 52 which opens both sidewardly and upwardly and is defined by a bottom surface 53 of wall 50 and a pair of generally upright side surfaces 54 and 55 of wall 50. More specifically, bottom surface 53 angles downwardly as same projects both inwardly and frontwardly, and side surfaces 54 and 55 are oriented substantially perpendicular to one another and transversely relative to bottom surface 53. Housing wall 50 has a generally upright inner surface 57 which adjoins a bottom surface 58, and also includes an upright intermediate wall 60 which extends transversely across the interior of hub 41 and has a pointed upper elongate edge 61 which extends across the entire extent of intermediate wall 60. Surfaces 57 and 58 and intermediate wall 60 together define a chamber 61A.

Wall structure of hub 41 additionally includes a plurality, and here three, of mounting structures 62, which in the illustrated embodiment are each of a cylindrical configuration so as to define respective mounting holes 63 which open upwardly for cooperation with cover 43 as discussed below. Further, and with reference to FIGS. 5, 6, 8 and 11, housing wall 50 of hub 41 includes a mounting structure 64 which is tubular and defines a lower mounting hole 65 and an upper hole or guide 66 which communicates with, and is an upper extension of, lower mounting hole 65. Mounting structure 64, as best shown in FIGS. 6 and 11, defines an inwardly projecting annular shoulder 67 which abuts the upper terminal end of channel member 42.

Referring to FIGS. 7-10 and 12, housing wall 50, at its front side adjacent locking arrangement 45, is formed so as to include a pair of clamping walls or members 68 and 69 disposed in opposed relation with one another. Clamping walls 68 and 69 are sidewardly spaced from one another to define a generally vertically oriented slot 70. Clamping wall 68 defines side surface 55 which faces outwardly and defines a portion of recess 52, an inner side surface 72 facing opposite side surface 55, and a through hole 71 which extends through the entire extent of clamping wall 68 and between surfaces 55 and 72. Clamping wall 69 defines an inner side surface 73 disposed in opposed relation with side surface 72 of clamping wall 68, which side surfaces 72 and 73 together define slot 70. Clamping wall 69, additionally defines an outer side surface 74 facing away from surface 73, which is configured as a cam surface as discussed further below.

Housing wall 50 defines a further recess 76 on the opposite side of hub 41 from recess 52. In this regard, recess 76 is generally semi-circular in configuration and opens both frontwardly and sidewardly, and is defined in part by outer side surface 74 of clamping wall 69. As mentioned above, outer side surface 74 functions as a cam surface, and angles inwardly as same projects downwardly within recess 76 (see FIGS. 10 and 12), such that a frontmost portion of clamping wall 69 effectively has a thickness which decreases as the wall 69 projects downwardly. Clamping wall 69 additionally defines a further outer side surface 78 located within recess 76 and disposed rearwardly of surface 74, which surface 78 also functions as a cam surface. Cam surfaces 74 and 78 are generally arcuate in shape when viewed from the side (i.e. in a direction along the central axis of recess 76). At the upper end of cam surface 74, clamping wall 69 is formed so as to define a generally flat and rearwardly facing stop surface 80, and likewise clamping wall 69 at the lower end of cam surface 78 is configured to define a frontwardly facing stop surface 81 which is generally vertically aligned with stop surface 80 and is vertically-downwardly spaced from stop surface 80. It will be appreciated that while cam surface 74 projects or angles inwardly as same projects downwardly from stop surface 80, cam surface 78 angles inwardly as same projects upwardly away from stop surface 81. Thus, cam surfaces 74 and 78 are inclined in opposite directions from one another.

Additionally, clamping wall 69 defines therein a through hole 83 which extends completely through wall 69, opens inwardly through surface 73 and opens outwardly through cam surfaces 74 and 78. Through hole 71 of clamping wall 68 and through hole 83 of clamping wall 79 are axially aligned with one another so as to together define a mounting orifice which cooperates with locking arrangement 45.

Figure 5:
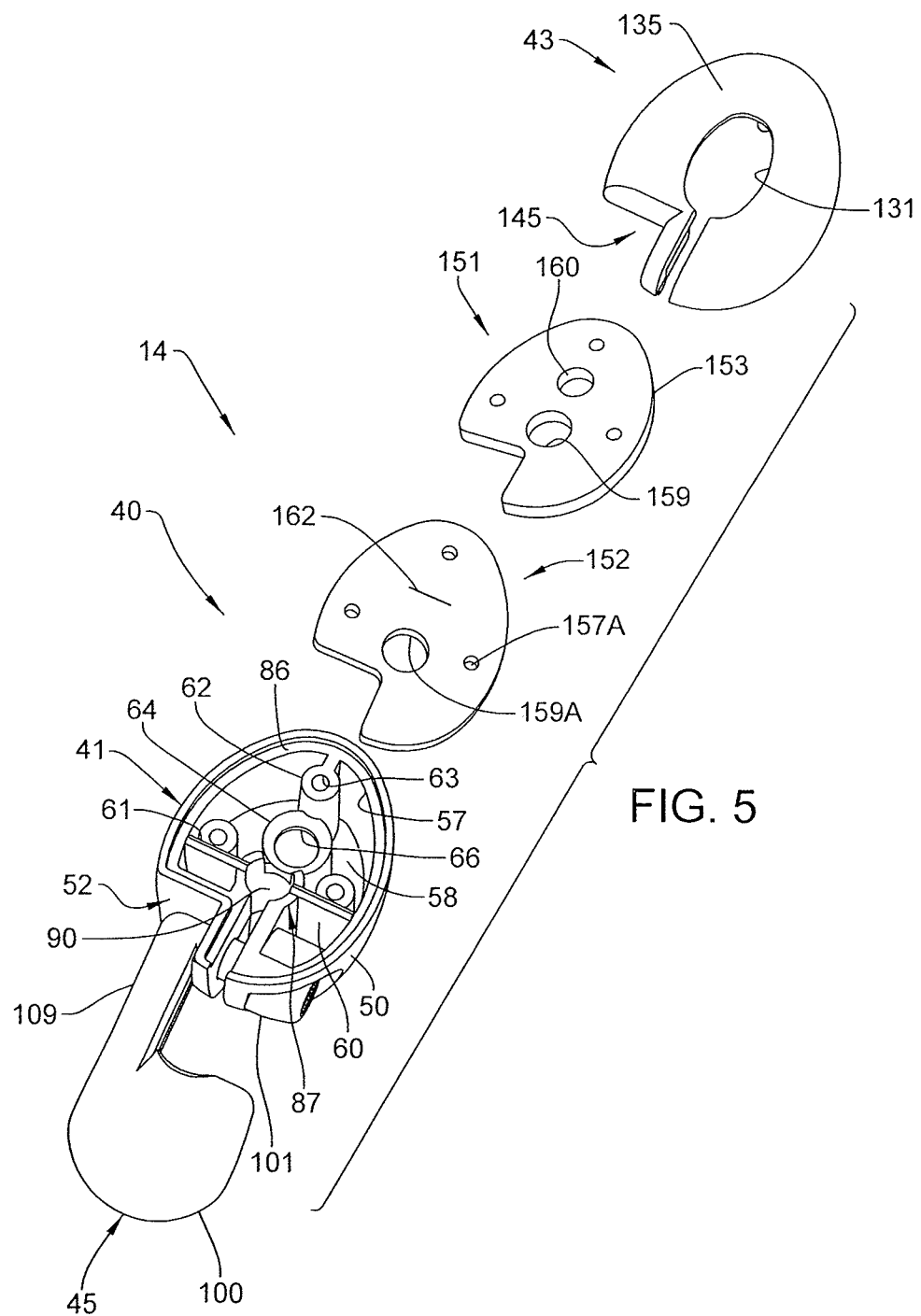
FIG. 5 is an exploded top perspective view of the access and positioning arrangement of FIG. 2.
Figure 6:
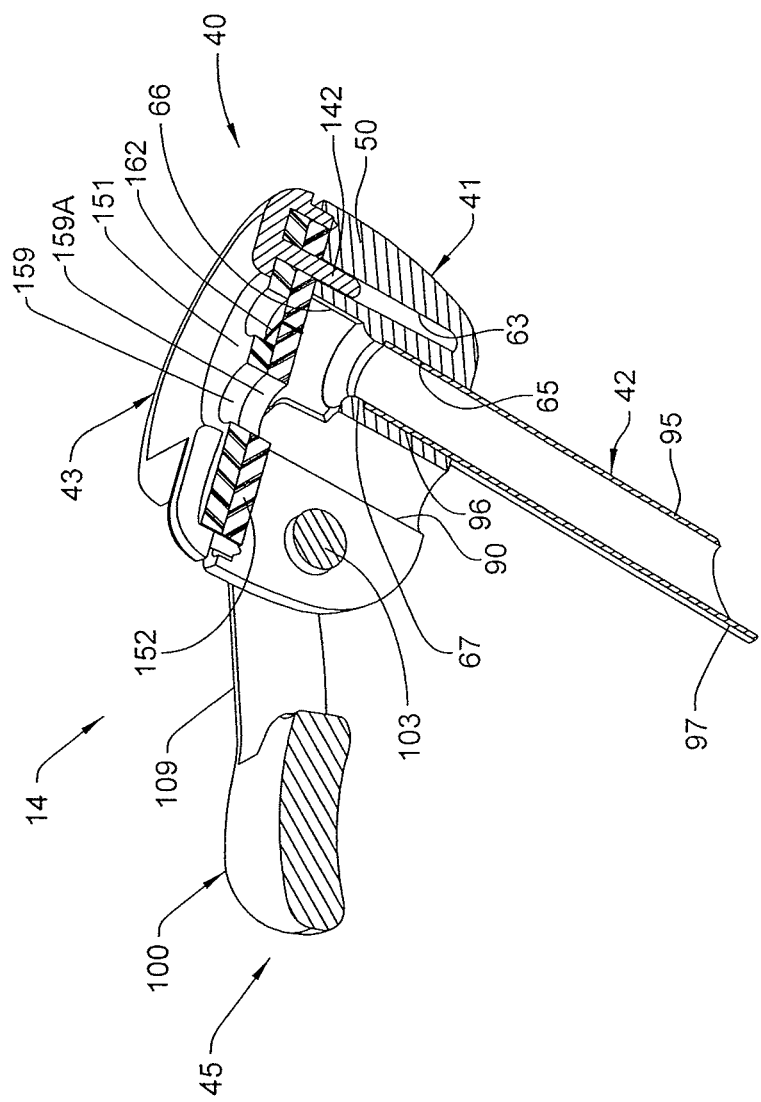
FIG. 6 is a cross-sectional view as seen generally along line 6-6 in FIG. 3.
Figure 12:
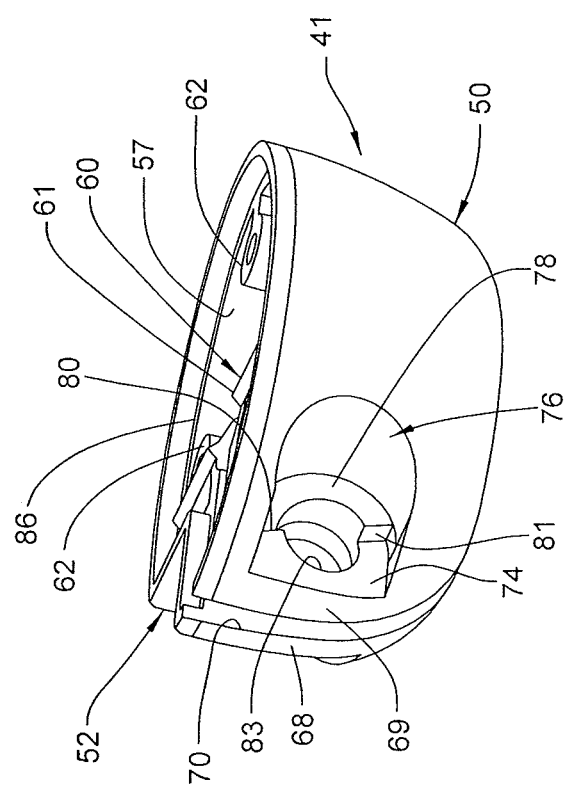
FIG. 12 is a side perspective view of the hub of the hub assembly of FIG. 7 without the channel member, which illustrates the cam surfaces of the hub.

Housing wall 50, as shown in FIGS. 5, 7 and 11, has an upper annular edge which is recessed so as to define an upwardly facing shoulder 86 which extends about the entire upper periphery of wall 50. Further, clamping walls 68 and 69 intersect with intermediate wall 60 and adjacent wall 60 are recessed outwardly relative to one another so as to form respective opposed sides of a semi-circular guide wall 87 having inwardly-facing and opposed arcuate surfaces 88 and 89 which together define a clamp opening 90. Clamp opening 90, as best shown in FIG. 5, is positioned so as to interrupt guide wall 60 at a mid-region thereof. Clamp opening 90 communicates at a front end thereof with slot 70, and when viewed from above or below as in FIGS. 8 and 9, slot 70 and opening 90 together have a key-hole shape. Clamp opening 90 extends through the entire vertical extent of hub 41 and opens both upwardly and downwardly for cooperation with cannula 13. Additionally, guide wall 87 is disposed sidewardly adjacent, and in the illustrated embodiment is adjoined to, mounting structure 64. As shown in FIG. 11, the central longitudinal axis A of clamp opening 90 formed by guide wall 87 and the central longitudinal axis B of co-extensive upper guide hole 66 and lower mounting hole 65 are at a slightly angled orientation relative to one another, and in the illustrated embodiment define an angle of 1-2°. This angled relation of axes A and B causes the lower end of channel member 42 when mounted within lower mounting hole 65 to be angled slightly towards the front of hub 41 as best shown in FIGS. 9 and 11.

In the illustrated embodiment, channel member 42 is constructed of a rigid material, such as stainless steel, and is defined by a tubular wall 95 having a proximal end 96 and a distal end 97. Channel member 42 is cut so that its distal end 97 is chamfered. Channel member 42 in the illustrated embodiment is fixed to hub 41 so that the proximal end 96 thereof is seated within lower mounting hole 65 and such that shoulder 67 abuts the terminal upper edge of proximal end 96 and serves as an upper stop for channel member 42. In the illustrated embodiment, the hub 41 is constructed of a rigid plastic and is joined to channel member 42 by overmolding.

Turning now to locking or clamping arrangement 45, and with reference to FIGS. 13-19, arrangement 45 generally includes an actuator or lever arm 100 which is generally C-shaped when viewed in plan view as in FIG. 13, and a cam cap 101 which serves to fix arm 100 to hub 41. Arm 100 includes at one end thereof a mounting pin 102 defined by a generally cylindrical arm segment 103, a necked-down segment 104 which defines a pair of flats 105 disposed on opposite sides of segment 104, and a further necked-down segment or tip 107 which defines the terminal inner end of arm 100, is adjoined to necked-down segment 104 and is generally rectangular in configuration. Arm 100 additionally includes an intermediate and elongated arm segment 109 joined at one end to the inner end of cylindrical arm segment 103 and at the opposite end to a generally plate-shaped finger grip 111 which defines the terminal outer end of arm 100.

Finger grip 111 has a surface 112 (which is referred to hereafter as a "lower" surface as same faces downwardly when the locking arrangement 45 is in the unlocked position as shown in FIG. 2), which lower surface 112 is of a shallow concave configuration so as to provide an ergonomic surface for the thumb, and an upper surface 113 which faces away from surface 112 and is of a slightly convex configuration so as to provide an ergonomic surface for the index finger disposed in opposed relation with the thumb of the user when manipulating arm 100. Finger grip 111, as shown in FIG. 17, is angled relative to intermediate arm segment 109, such that when arm 100 is installed on hub 41, arm 100 is easily manipulated by the surgeon. Further, finger grip 111 has an outer and generally rounded peripheral edge 114 which is generally semicircular when viewed from above or below, and an inner peripheral edge 115 which extends between and interconnects edge 114 and intermediate arm segment 109. Finger grip 111 is spaced from and is substantially parallel to mounting pin 102, and is oriented substantially perpendicular to intermediate arm segment 109.

Turning now to cam cap 101 of locking arrangement 45, and with reference to FIGS. 13, 14 and 18, same is defined by an outer and generally cup-shaped wall 117. Wall 117 is configured so as to define a bore 118 which extends completely through the entire extent of cam cap 101. Bore 118 is of a stepped configuration, and is defined by a bore section 120 which opens sidewardly outwardly through wall 117 and is of a generally rectangular configuration so as to conform to the rectangular configuration of tip 107 of arm 100. Bore 118 is additionally defined by a bore section 122 which is joined to and extends away from bore section 120 so as to open sidewardly through the opposite side of wall 117 from bore section 120. A shoulder 123 extends about and defines the junction between bore sections 120 and 122. Bore section 122 and shoulder 123 have a configuration which corresponds to necked-down segment 104 of arm 100, wherein shoulder 123 engages or abuts a terminal and end-facing outer peripheral edge 105A of necked-down segment 104 and flats 105 thereof engage in bore section 122 in a keyed manner which prevents rotation of arm 100 relative to cap 101.

On the end of cam cap 101 opposite the end where bore section 120 opens outwardly, outer wall 117 is configured so as to define a pair of cam surfaces 124 and 125 which are semi-circular when viewed from above and surround and define the opening of bore section 122. Cam surfaces 124 and 125 have smooth and gradually ascending ramp-like configurations, wherein the lowermost end of cam surface 124 adjoins an uppermost or elevated end of cam surface 125 via a generally flat stop face 127. Stop face 127 defines the intersection of cam surfaces 124 and 125, and is oriented generally transversely thereto. Further, the uppermost or elevated end of cam surface 124 adjoins the lowermost end of cam surface 125 via a further generally flat stop face 128, which stop face 128 defines the intersection of cam surfaces 124 and 125 opposite stop face 127 and is generally transversely oriented relative to surfaces 124 and 125. Cam surfaces 124 and 125 are of substantially the same arc-length such that stop faces 127 and 128 are on diametrically opposite sides of cam cap 101. Further, stop faces 127 and 128 are coplanar with one another.

Arm 100 is assembled to hub 41 by inserting mounting pin 102 into recess 52 of hub 41 and through holes 71 and 83 of clamping walls 68 and 69 so that segment 103 extends through holes 71 and 83, and so that segment 104 and tip 107 project outwardly from hole 83. Cam cap 101 is then installed onto and over arm segment 104 and tip 107 so that tip 107 engages and is keyed within bore section 120, and so that arm segment 104 with its flats 105 is engaged and keyed within bore section 122. As mentioned above, shoulder 123 of cap 101 abuts the edge 105A of necked-down segment 104 when arm 100 is installed on hub 41 and cam cap 101 is in position on arm 100. When installing cam cap 101 onto arm 100, cam cap 101 is inserted into recess 76 of hub 41, and specifically cap 101 is positioned so that cam surface 124 of cap 101 is rotationally aligned with cam surface 78 of clamping wall 69, and so that cam surface 125 is rotationally aligned with cam surface 74 of clamping wall 69. In this position, stop surface 128 of cap 101 is disposed in engaged and face-to-face and opposed relation with stop surface 80 of clamping wall 69, and stop surface 127 of cap 101 is engaged and in face-to-face opposed relation with stop surface 81 of clamping wall 69.

In the illustrated embodiment, arm 100 and cam cap 101 are constructed of rigid plastic and are formed by molding, and adhesive may be applied to either cam cap 101 (for example in recess 118) or onto the arm segment 104 before installing cam cap 101 on arm 100 as described above to provide a secure connection between cam cap 101 and arm 100.

Figure 21:
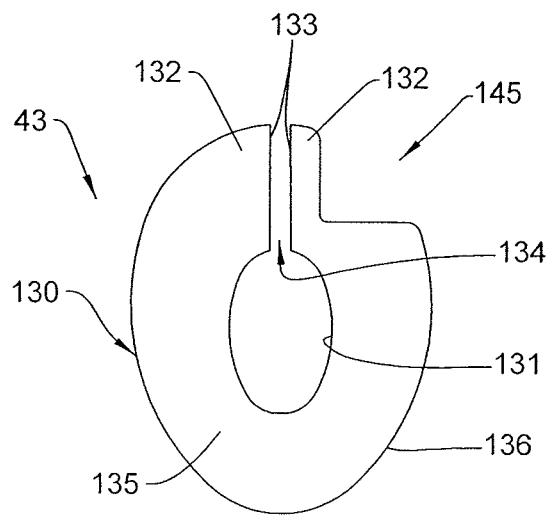
FIG. 21 is a top view of the cover of FIG. 20.
Figure 20:
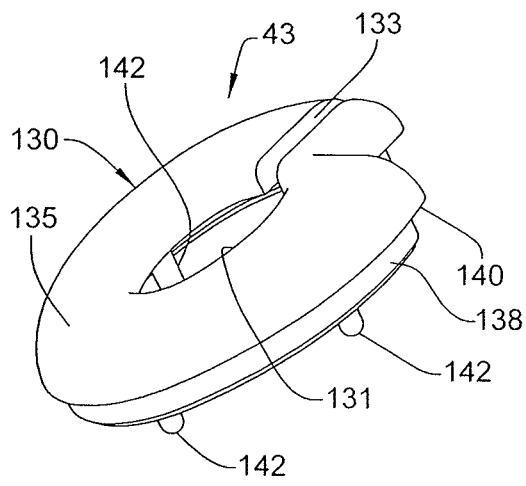
FIG. 20 is an enlarged top and front perspective view of the cover of the hub assembly of FIG. 2.
Figure 22:
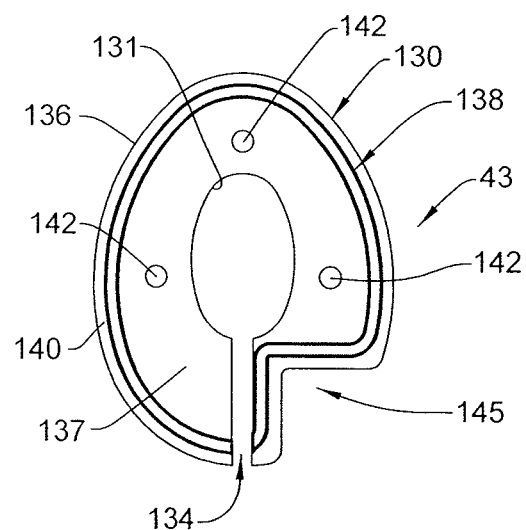
FIG. 22 is a bottom view of the cover of FIG. 20.
Figure 23:
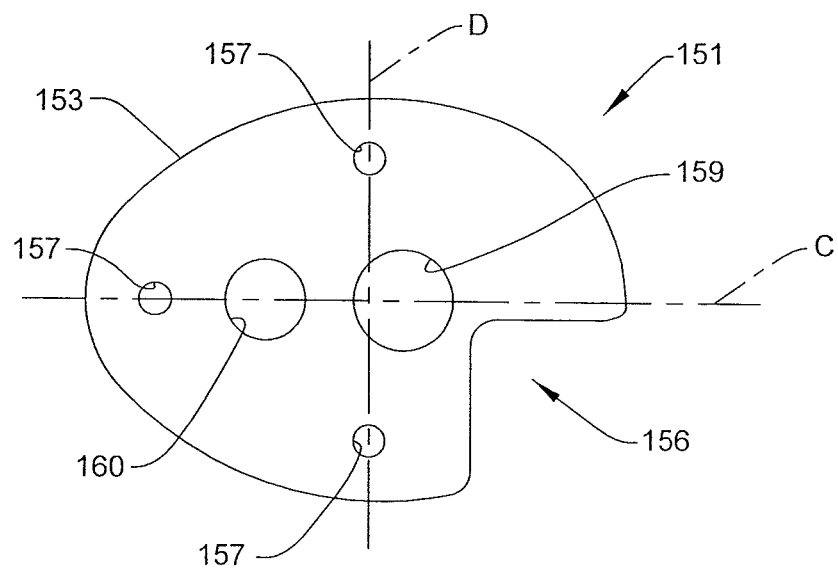
FIG. 23 is an enlarged top view of the top seal of the hub assembly of FIG. 2.

Turning now to cover or lid 43 of hub assembly 40, and with reference to FIGS. 20-22, lid 43 is of a generally elliptical shape when viewed from above so as to conform with the shape of the upper end of hub 41, and is defined by a housing wall 130 which is annular so as to define a generally elliptically-shaped opening 131. Housing wall 130 is split or divided at one end thereof so as to define a pair of terminal ends 132 including respective terminal end faces 133 which are spaced from one another to define a slot 134 therebetween. Slot 134 extends sidewardly through the entire extent of housing wall 130 so as to open both outwardly and inwardly for communication with opening 131.

Housing wall 130 defines an upper surface 135 which in the illustrated embodiment is generally flat in an area immediately surrounding opening 131, and is of a rounded configuration sidewardly or outwardly of this flat area of upper surface 135 so as to have a downwardly-curving configuration along an outer periphery 136 of lid 43. Housing wall 130 includes a lower surface 137 opposite upper surface 135, and a mounting flange 138 which projects downwardly from lower surface 137. Mounting flange 138, as shown in FIG. 22, extends in an annular manner about the lower surface 137 of lid 43, and is spaced inwardly from periphery 136 such that a shoulder 140 is defined outwardly of flange 138, which shoulder 140 is generally perpendicular to flange 138. Mounting flange 138 is discontinued at slot 134. Further, a plurality, and here three, of mounting elements 142 in the shape of posts or pegs are cantilevered downwardly from lower surface 137 of lid 43. Mounting pegs 142 are oriented in spaced relation with one another about opening 131 in positions corresponding with the positions of mounting structures 62 of hub 42. Further, housing wall 130 defines therein a generally corner-shaped and inwardly-projecting recess 145 adjacent slot 134, which recess 145 conforms in shape to recess 52 of hub 41.

Hub assembly 40 additionally includes a seal arrangement including an upper seal 151 and a lower seal 152, as shown in FIGS. 5, 6, 23 and 24. Upper and lower seals 151 and 152 are of a generally flat configuration, are of a generally elliptical shape when viewed from above or below, and are constructed of an elastomeric material. Upper seal 151 has an outer periphery 153 which defines a generally corner-shaped recess 156 conforming in shape to recess 52 of hub 41 and to recess 145 of lid 43. Seal 151 defines therein a plurality, and here three, of mounting holes 157 disposed in spaced-apart relation with one another inwardly of periphery 153 and in positions corresponding to mounting structures 62 of hub 41 and mounting pegs 142 of lid 43. Seal 151 also includes an enlarged hole 159 adjacent recess 156 and a smaller hole 160 disposed sidewardly of hole 159. Holes 159 and 160, and one mounting hole 157, are aligned and with one another along, and are centered on, a central longitudinal axis C of seal 151, and the remaining two mounting holes 157 are disposed on opposite sides of enlarged hole 159, are aligned with one another along, and are centered on, a central transverse axis D of seal 151.

Figure 24:
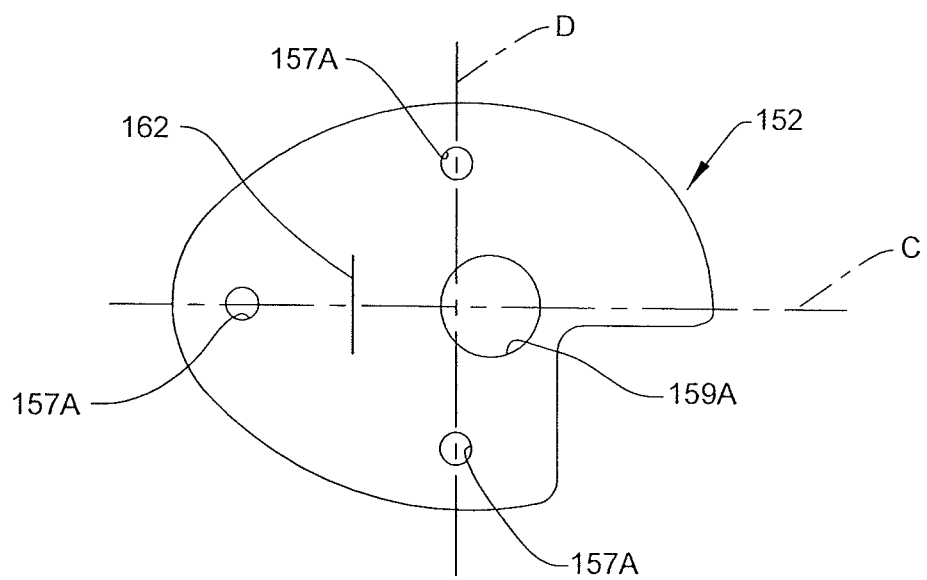
FIG. 24 is an enlarged top view of the bottom seal of the hub assembly of FIG. 2.

Lower seal 152 shown in FIG. 24 is identical to upper seal 151, except that lower seal 152 includes a slit 162 in place of smaller mounting hole 160 of upper seal 151. Accordingly, the components of lower seal 152 which are identical to components of upper seal 151 are identified with the same reference numbers, plus an "A". Slit 162 extends generally parallel to transverse axis D, and has a transverse dimension approximately the same as the diameter of hole 159A.

With reference to FIG. 5, seals 151 and 152 are assembled to hub 41 by inserting lower seal 152 into the open upper end of hub 41 and atop shoulder 86 thereof so that slit 162 is aligned with upper guide hole 66, mounting holes 157A are aligned with mounting structures 62, and so that opening 159A is aligned with opening 90 of hub 41. Upper seal 151 is then positioned atop lower seal 152 so that opening 159 is aligned with opening 159A, opening 160 is positioned over slit 162, and so that mounting holes 157 are positioned over mounting holes 157A. Lid 43 is then positioned atop upper seal 151 and mounting pegs 142 are aligned with and inserted into and through the aligned pairs of holes 157 and 157A of seals 151 and 152 and into mounting holes 63 of the respective mounting structures 62 of hub. Lid 43 may be fixed to hub 41 via suitable locking structures which cooperate between mounting pegs 142 and mounting structures 62, via adhesive provided between these components, or other suitable fixation methods. With seals 151 and 152 assembled to hub 41 and sandwiched between lid 43 and shoulder 86 of hub 41, the upper pointed edge 61 of intermediate wall 60 serves to compress seals 151 and 152 between lid 43 and hub 41 and also locks seals 151 and 152 securely in place. The engagement of edge 61 with seal 152 also serves to prevent fluid from hub chamber 61A from entering into the open area of hub 41 adjacent locking arrangement 45 and on the opposite side of intermediate wall 60 from chamber 61A.

Figure 25:
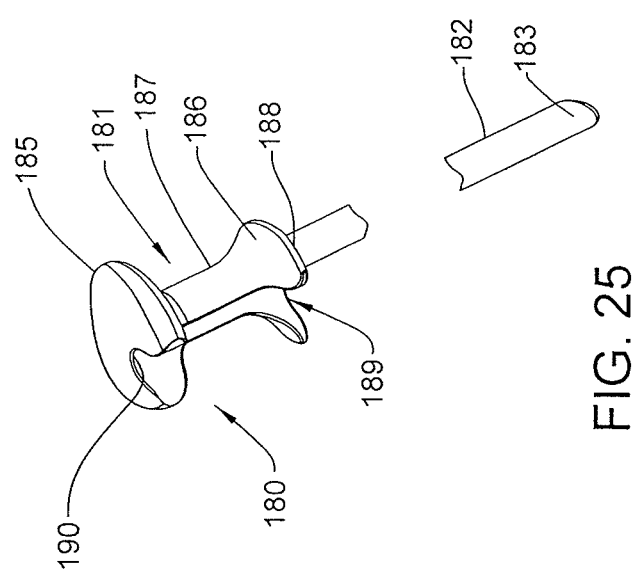
FIG. 25 is a side perspective view of an obturator.

FIG. 25 illustrates an obturator 180 which may be utilized in conjunction with the access and positioning arrangement 14 according to the invention. Obturator 180 in the illustrated embodiment is elongated in shape and includes an upper terminal end 181 which defines a handle, and an elongated shaft 182 which projects outwardly from handle 181. Shaft 182 has a lower terminal end 183 which is chamfered so as to correspond with the chamfered lower end 97 of channel member 42. Handle 181 of obturator 180 in the illustrated embodiment is generally of an hourglass configuration when viewed from the side, which configuration is defined by an upper rounded flange 185 and a lower rounded flange 186 spaced from upper flange 185 by an intermediate segment 187. Intermediate segment 187 interconnects upper and lower flanges 185 and 186 and is of a lesser diameter or width than upper and lower flanges 185 and 186. Further, lower flange 186 has a lowermost and downwardly facing surface 188 which is generally flat or planar. Handle 181 of obturator 180 defines therein a sidewardly-opening channel 189 which extends through the entire vertical or longitudinal extent of handle 181 and causes the upper and lower flanges 185 and 186 to be generally U-shaped when viewed from above. Additionally, a sidewardly-facing surface 190 of handle 181 which defines the inner extent of channel 189 is rounded when viewed in transverse cross-section along the entire longitudinal extent of channel 189. In the illustrated embodiment, the shaft 182 of obturator 180 is of a length which is approximately equal to the length of the channel member 42 (i.e. the length of the part of member 42 which is located exteriorly of hub 41) plus the vertical height of hub 41 and cover 45.

Figure 19:
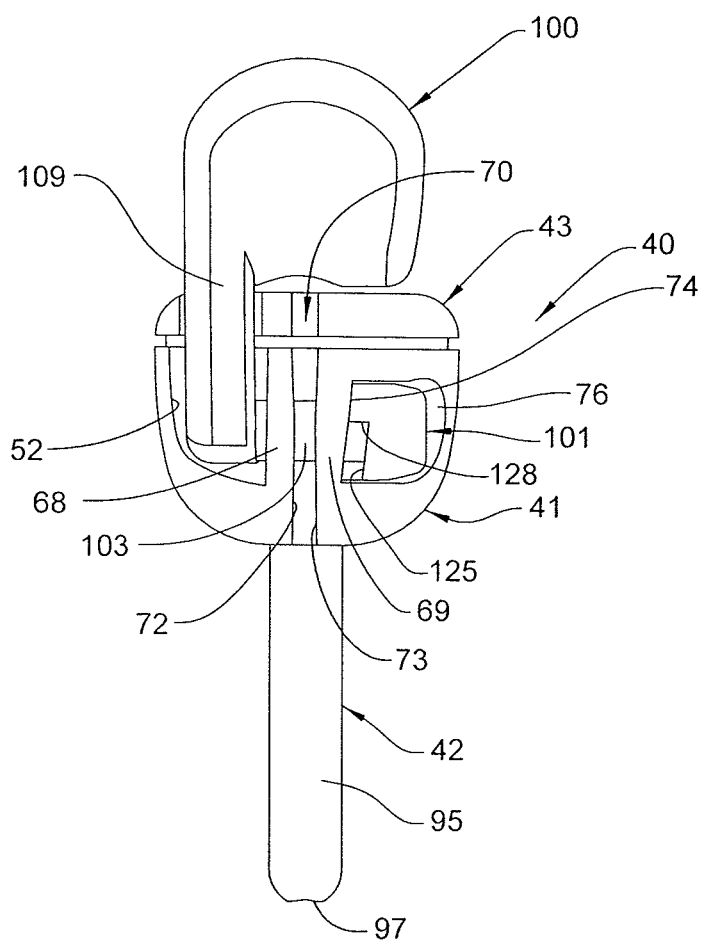
FIG. 19 is an enlarged front view of the hub assembly of FIG. 2, with the locking arrangement in the locked or clamped position.

With reference to FIGS. 2 and 19, locking arrangement 45 is movable between a locked or clamped position as shown in FIG. 19 and an unlocked position as shown in FIG. 2. In the unlocked position in FIG. 2, arm 100 is positioned generally transversely relative to channel member 42. Further, in the unlocked position, stop surface 128 of cap 101 is positioned closely adjacent stop surface 81 located within hub recess 76, and stop surface 127 of cap 101 is positioned closely adjacent stop surface 80. Stop surfaces 80 and 81 serve to prevent further downward rotational movement of arm 100 from the position shown in FIG. 2. In this position of arm 100 of locking arrangement 45, the slot 70 defined between clamping walls 68 and 69 of hub 41 is at its maximum dimension as measured transversely between the opposed surfaces 72 and 73 of walls 68 and 69.

In order to place locking arrangement 45 in its locked position, finger grip 111 of arm 100 is gripped by the surgeon and arm 100 is rotated upwardly from the position shown in FIG. 2 into the position shown in FIG. 19, so that intermediate arm segment 109 is vertically positioned against surfaces 54 and 55 which define hub recess 52, edge 115 of finger grip 111 is located closely adjacent cover 45, and finger grip 111 is oriented above, and generally perpendicularly relative to, cover 45. As arm 100 is rotated upwardly in this manner from the position shown in FIG. 2, cam surface 125 of cap 101 is rotated upwardly, causing the elevated end of cam surface 125 to come into full engagement with the widest (i.e. upper) portion of cam surface 74 as defined by clamping wall 69 of hub 41, and likewise causing the elevated end of cam surface 124 to come into full engagement with the widest (i.e. lower) portion of cam surface 78 as defined by clamping wall 69. The positioning of the cam surfaces 124 and 125 of cap 101 in the above locations relative to cam surfaces 74 and 78 causes deflection of clamping wall 69 inwardly towards clamping wall 68, which decreases the distance between the opposed surfaces 72 and 73 and the width of slot 70, and effectively causes inward movement of surface 88 of hub guide wall 87 towards opposed surface 89 which serves to reduce the diameter or transverse dimension of clamp opening 90.

The locking arrangement 45 is returned to its unlocked position simply by rotating arm 100 back downwardly from the position shown in FIG. 19 to the position shown in FIG. 2 which causes movement of clamping wall 69 away from clamping wall 68 and effectively increases the diameter or transverse dimension of clamp opening 90.

Figure 26:
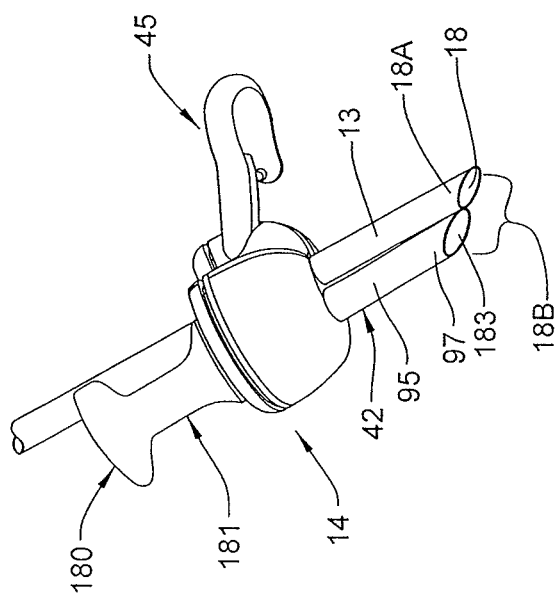
FIG. 26 is an enlarged and fragmentary view of the access and positioning arrangement with the obturator of FIG. 25 mounted thereon and illustrating the positions of the distal ends of the working channel and the endoscope assembly when utilized to enlarge an incision in the patient.

One method of using the surgical tool arrangement 10 according to the invention is described below with reference to FIGS. 1 and 26. The endoscope 15 is initially not installed within cannula 13, and instead an obturator (not shown) configured for cooperation with cannula 13 is installed within cannula 13 so as to occlude the interior channel thereof. Additionally, the obturator 180 is installed on the access and positioning arrangement 14 by inserting the distal end 183 into and through the aligned opening 160 in upper seal 151 and slit 162 of lower seal 152, into and through upper guide hole 66 of hub mounting structure 64, and into and through the channel member 42. The obturator 180 is rotationally positioned relative to hub assembly 40 so that chamfered distal end 183 is essentially flush with chamfered distal end 97 of channel member 42, and so that lower surface 188 of handle 181 is positioned on the upper surface 135 of cover 43 with channel 189 of obturator 180 in vertically aligned relation with openings 159 and 159A of seals 151 and 152 as well as clamp opening 90 of hub 41.

The access and positioning arrangement 14 with obturator 180 mounted thereon as described above and with locking arrangement 45 in the unlocked position as shown in FIG. 2 is then installed on the cannula 13. Specifically, distal end 18A of cannula 13 is aligned with and inserted into the upper end of the obturator channel 189, into and through openings 159 and 159A of seals 151 and 152, and into and through clamp opening 90. The access and positioning arrangement 14 is then moved longitudinally along and relative to the cannula 13 towards the proximal end 19 thereof, and locking arrangement 45 may be moved into the locking position as shown in FIG. 19 so as to maintain the arrangement 14 in the desired position relative to cannula 13. A puncture is made through the patient's skin at the surgical site with a scalpel or other suitable tool, and the distal end 18A of the cannula 13 is inserted through the puncture and into the surgical site. The obturator is then removed from the cannula 13, the endoscope 15 is installed within cannula 13, and at this juncture the surgeon typically conducts a diagnostic "tour" with the endoscope 15 in order to view the surgical site. The locking arrangement 45 is moved into the unlocked position, and the access and positioning arrangement 14 is moved along the cannula 13 and towards the distal end 18A thereof until the distal end 97 of the channel member 42 is positioned immediately adjacent the distal end 18A of the cannula 13 as shown in FIG. 26, so that the chamfered distal ends 18A and 97 together define an essentially continuous chamfered distal tool edge 18B which can be utilized to enlarge the incision. In this regard, due to the angular orientation the central axis B of the channel member 42 relative to the central axis A of the clamping opening 90, the distal end 97 of the channel member 42 is in contacting relation with the distal end 18A of cannula 13 as shown in FIG. 26. This contacting arrangement prevents tissue from entering between the channel member 42 and the cannula 13 during insertion of the arrangement into the patient.

The arrangement 14 and cannula 13 are then advanced into the surgical site, wherein the lower surface of the hub 41 of the arrangement 14 will eventually rest atop or be positioned adjacent (i.e. spaced from) the skin of the patient at the surgical site. The cannula 13 and endoscope 15 are positioned at the proper depth within the patient, and the arm 100 of the locking arrangement 45 is then placed in the locked position so as to fix the position of the cannula 13 and endoscope 15 relative to arrangement 14 and/or relative to the patient if the hub 41 of the arrangement 14 is positioned directly atop the portal defined in the patient.

The obturator 180 is then removed from the access and positioning arrangement 14, and a punching tool or other suitable instrument (not shown) is inserted through arrangement 14, and specifically through channel member 42 and into the surgical site, in order to remove large pieces of tissue from the surgical site. The punching tool is then removed from channel member 42. With reference to FIG. 1, the surgical instrument 12, in the illustrated embodiment a shaver, is then inserted into the channel member 42. Specifically, the distal end of outer tube 31 is inserted into the arrangement 14 through opening 160 and slit 162 of seals 151 and 152, into hole 66 of hub 41 and downwardly through channel member 42. The distal end of outer tube 31 of surgical instrument 12 is then positioned within the field of view of the endoscope 15. In this regard, the distal end 18 of the endoscope 15 has a field of view of approximately 80-120 degrees, which is the total included angle centered on the direction of view of the endoscope 15, which direction of view is perpendicular to the plane of the chamfered distal end 18. The chamfered distal end 18 must face at least partially towards the distal end of the instrument 12 at the surgical site, so that the instrument 12 will be positioned within the field of view of the endoscope 15. The working or distal end of the surgical instrument 12 must be positioned within this defined field of view of the endoscope 15 in order for the surgeon to be able to properly view the operation of instrument 12 at the surgical site. The defined position of the channel member 42 of arrangement 14 relative to the endoscope 15, the position of which endoscope 15 is fixed via its engagement within clamping opening 90 of arrangement 14, allows the surgeon to readily and easily insert the surgical instrument 12 via channel member 42 into the surgical site and directly into the field of view of the endoscope 15. Once the surgical instrument 12 is positioned within arrangement 14 and in the field of view of the endoscope 15, various operations can be carried out at the surgical site as needed. When a shaver used as the surgical instrument, the rotational position of outer tube 31 of instrument 12 can be varied as necessary within channel member 42 by manipulating the handpiece within which hubs 30 and 32 are mounted, which will effectively change the rotational position of the cutting window 33 of tube 31 at the surgical site. Additionally, the arrangement 14, once endoscope 15 is fixed to hub 41, allows the user to rotate the working channel 42 relative to the endoscope 15 which maintains the surgical instrument 12 within the ideal portion of the field of view.

Typically, it is undesirable to have the operative surgical instrument 12 directly in front of the endoscope optics at the distal end 18 of the endoscope 15, since the surgical instrument 12 will block the field of view. It is also undesirable to have the operative surgical instrument 12 directly opposite the endoscope optics, since the surgical instrument 12 will not be visible to the surgeon. Further, it is desirable to be able to adjust the position of the operative surgical instrument 12 in the left and right portions of the field of view of the endoscope 15.

The access and positioning arrangement 14 according to the invention thus serves multiple purposes. In this regard, the arrangement 14 serves to define an area which allows direct access to the surgical site via the positioning of the hub 41 of the arrangement 14 adjacent to, and in some cases directly on the skin surrounding the portal defined in the patient, and defines access openings or channels in the form of clamping hole 90 for cannula 13/endoscope 15, and opening 66 and channel member 42 for surgical instrument 12. The arrangement 14 allows engagement and fixation of the cannula 13/endoscope 15 within the clamping hole 90 via the locking arrangement 45, so that the cannula 13/endoscope 15 can be locked at the desired depth and rotational position relative to arrangement 14 and/or within the surgical site. The opening 66 and channel member 42 thus provide a defined pathway into the surgical site and into the field of view of the endoscope 15. Additionally, these access openings 90 and 66 defined in arrangement 14 are sealed via upper and lower seals 151 and 152, so that any fluids at or around the surgical site are prevented from escaping or leaking outwardly of the arrangement 14. In this regard, the clamping opening 90 is sized so as to be able to accept a standard cannula/endoscope, and seal openings 159 and 159A are sized so as to be somewhat smaller than the diameter of the clamping opening 90 so that the seals 151 and 152 adequately seal around the diameter of the cannula/endoscope. Further, the diameter of opening 160 is sized so as to be somewhat smaller than the shaft diameter of typical surgical instruments to provide an adequate upper seal, and the slit 162 serves as a secondary seal in that same automatically seals around the instrument as same is inserted therethrough. As mentioned above, the intermediate wall 60 of hub 41 with its pointed upper edge 61 which engages and compresses seals 151 and 152 serves to seal off chamber 61A, which chamber 61A surrounds the surgical instrument 12 when engaged with the arrangement 14, which will prevent or at least minimize leaking of fluids into the area of the hub 41 surrounding or adjacent the locking arrangement 45. Further, the use of two vertically-stacked seals 151 and 152 ensures maximum sealing of the upper end of hub assembly 40.

Figure 27:
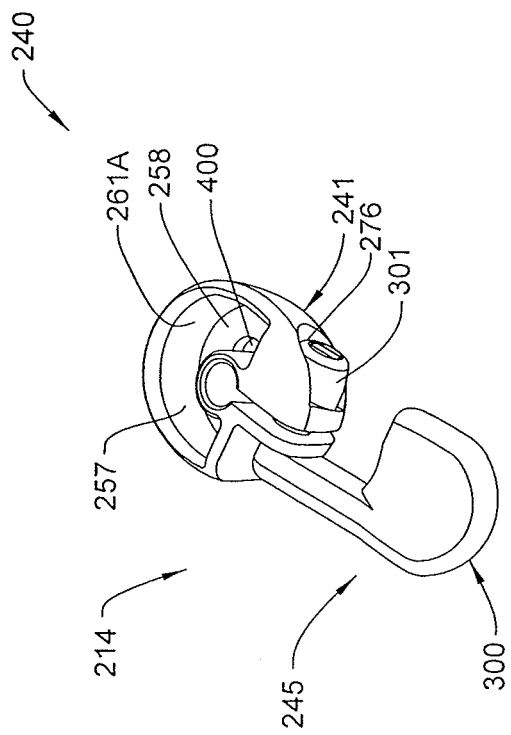
FIG. 27 is a top and front perspective view of a second embodiment of the access and positioning arrangement according to the invention.
Figure 28:
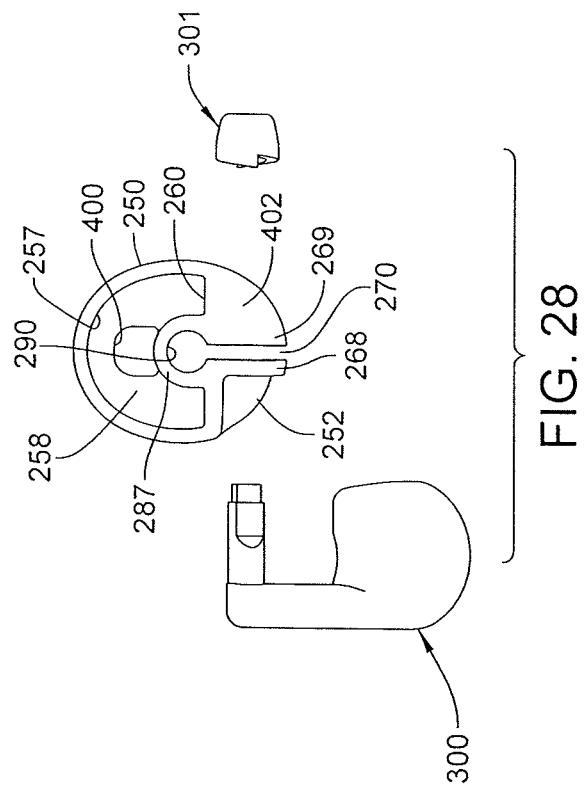
FIG. 28 is an exploded top view of the access and positioning arrangement of FIG. 27.
Figure 29:
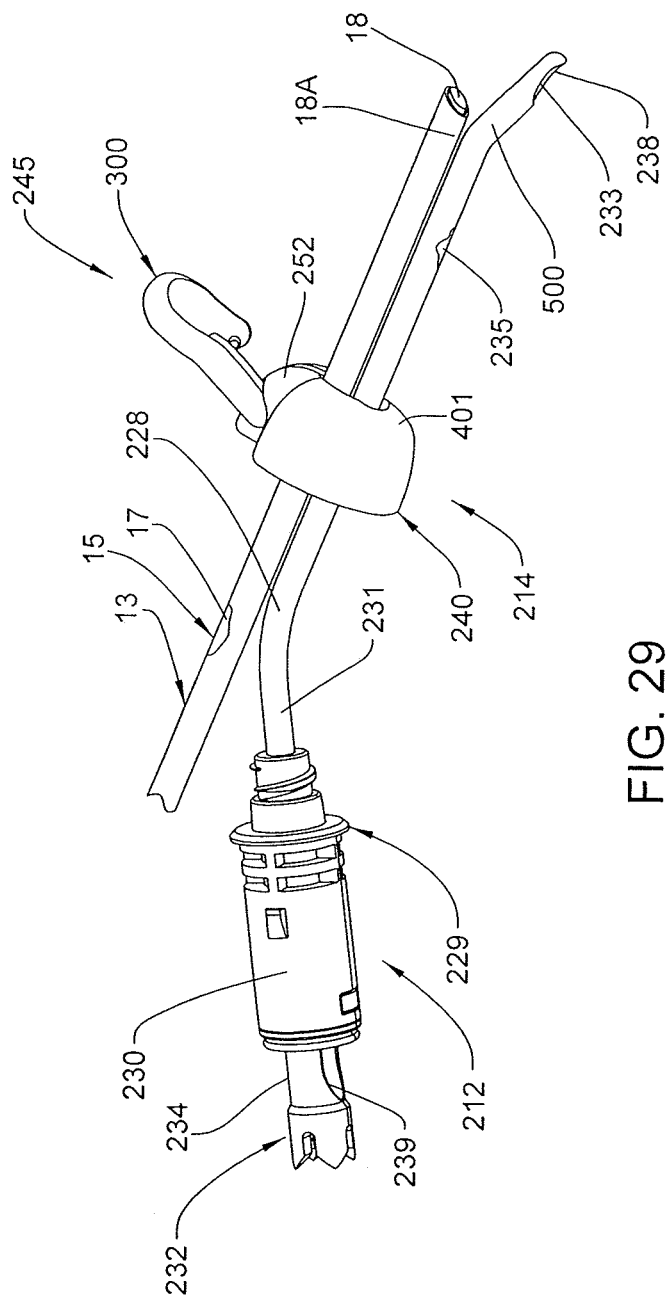
FIG. 29 is an illustration of the second embodiment of the access and positioning arrangement in use with two surgical instruments.

A second embodiment of the access and positioning arrangement is illustrated in FIGS. 27-29. The access and positioning arrangement 214 according to the second embodiment is similar to the access and positioning arrangement 14, and thus components of arrangement 214 which are identical or similar to components of arrangement 14 will be identified with the same reference numbers, plus 200.

Arrangement 214 includes a hub assembly 240 including a generally hollow hub 241 and a locking or actuator arrangement 245 mounted on hub 241. Access and positioning arrangement 214, unlike arrangement 14, does not include a working channel 42, lid 43 or seals 151 and 152. Hub 241 is defined by a wall structure including a generally rounded and upwardly-opening outer housing wall 250. Housing wall 250 includes recess 252 for locking arrangement 245, and a generally upright inner surface 257 which adjoins an upwardly-facing bottom surface 258. Housing wall 250 additionally includes an intermediate wall 260 which extends across the interior of hub 241. Wall 260 and inner and bottom surfaces 257 and 258 together define an upwardly-opening and generally semi-circular chamber 261A.

Arrangement 214, in contrast to arrangement 14 which includes tubular mounting structure 64, includes an opening 400 defined in bottom surface 258 of housing wall 250, which opening 400 extends completely through a bottom portion 401 of housing wall 250. Housing wall 250, at its front side is formed to include opposed clamping walls 268 and 269 which are sidewardly spaced from one another to define a generally vertically oriented slot 270. Additionally, housing wall 250 defines a recess 276 on the opposite side of hub 241 from recess 252. Clamping wall 269 and recess 276 of housing wall 250 of arrangement 214 include the same cam configuration as arrangement 14. As arrangement 214 includes no cover or lid as does arrangement 14 with its lid 43, housing wall 250 of hub 241 is configured with an upper wall portion 402 which is positioned above or in overhanging relation with recess 276. Clamping walls 268 and 269, as in the prior embodiment, intersect with wall 260 and adjoin one another to form a generally circular guide wall 287 which defines clamp opening 290 which communicates with slot 270. Clamp opening 290 extends through the entire vertical extent of hub 241 and opens both upwardly and downwardly through bottom portion 401 of housing wall 250.

Arrangement 214 additionally includes locking or actuating arrangement 245 which is mounted on hub 241 and operates in the same manner as arrangement 45.

Access and positioning arrangement 214 is intended for use in surgical procedures in conjunction with surgical instruments or tools which include particular curvatures, such as surgical instrument 212 shown in FIG. 29. Instrument 212 is similar to instrument 12 discussed above, and components of instrument 212 which are similar or identical to components of instrument 12 are identified with the same reference numbers, plus 200. Surgical instrument 212, in addition to having a proximal bend 228 in outer tube 231, includes a distal bend 500 in outer tube 231 located just proximally of window 238. When an instrument of the type with a distally-bent portion is needed for a surgical procedure, the arrangement 214 will easily allow insertion of the instrument 212 into and through opening 400 in hub 241 due to the lack of a channel member similar to channel member 42. Thus, with cannula 13 installed within clamping opening 290 as discussed above relative to access and positioning arrangement 14, instrument 212 can be more freely manipulated with respect to the angle of deviation of the instrument 212 both proximally where instrument 212 engages within clamping opening 290 and distally of the hub assembly 240, which allows more flexibility when positioning the instrument 212 at the surgical site. It will be appreciated that other tools may be utilized in conjunction with arrangement 214 in addition to the surgical instrument 212 described above. For example, a shaver with only a single bend located adjacent the distal end thereof or a punch, RF probe, burr or drill with a bend located proximally and/or distally.

The access and positioning arrangement 214 according to this embodiment is utilized primarily for preventing enlargement or tearing of the incision or portal defined in the patient which provides access to the surgical site, and to maintain a fixed and spaced relation between the two instruments being utilized during the surgery.

It will be appreciated that access and positioning arrangements 14, 214 may include other types of locking or clamping arrangements in place of locking arrangement 45, 245 which serve to fix the position of the instrument located within hub opening 90, 290. For example, the locking arrangement may include a set screw which is mounted in a threaded orifice defined in a portion of hub 41, 241 such that when the set screw is screwed into hub 41, 241, the screw is brought into engagement with the instrument located within opening 90, 290. In this regard, the terminal end of set screw mounts thereon a protective cap, made of plastic or a resilient material for example, which directly engages the instrument so as to prevent damage to same.

As a further alternative to locking arrangement 45, 245, the hub 41, 241 can be provided with a threaded opening which extends through the respective opposed clamping walls 68, 268 and 69, 269 of hub 41 in place of openings 71 and 78, which threaded opening receives therein a threaded fastener provided with a knob on an outer terminal end thereof. The user utilizes the knob to rotate and advance the fastener into the threaded opening of the hub 41, 241 to cause the clamping walls 68, 268 and 69, 269 to move toward one another and effectively lock the instrument within opening 90, 290 of hub 41, 241.

Figure 32:
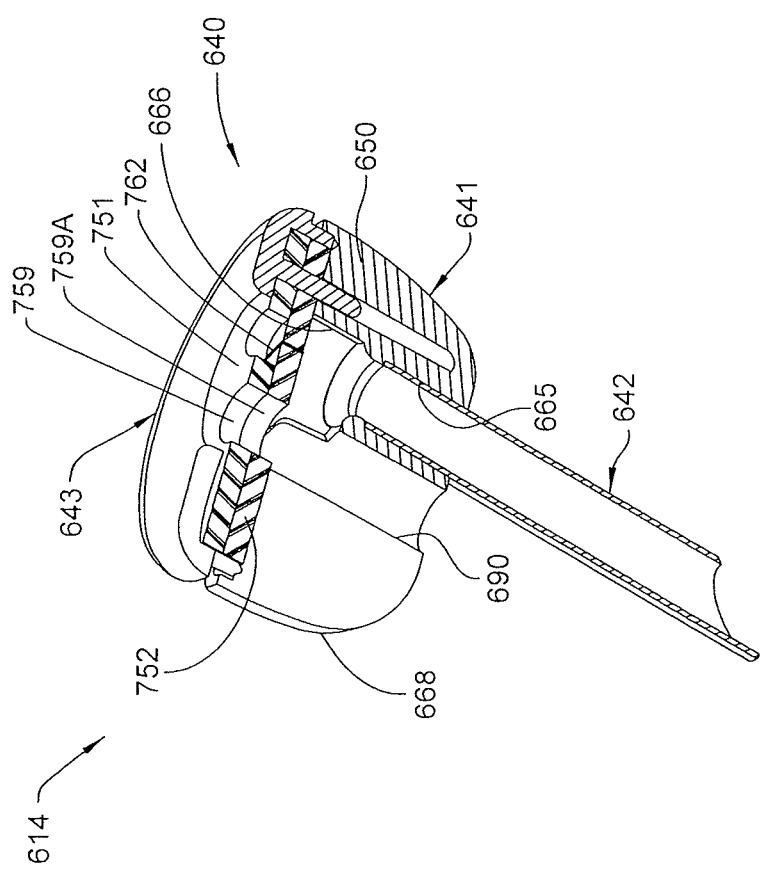
FIG. 32 is a cross-sectional view as seen generally along line 32-32 in FIG. 31.

A further or third embodiment of the access and positioning arrangement is illustrated in FIGS. 30-32. Components which are identical or similar to components of the access and positioning arrangement 14 discussed above are provided with the same reference numbers, plus 600. Arrangement 614 includes a hub assembly 640 including a generally hollow hub 641, a working channel 642 which is fixed to and projects from a bottom of hub 641, and a lid or cover 643 which closes off the open upper end of hub 641. Unlike arrangement 14, arrangement 614 does not include a locking arrangement 45, and outer housing wall 650 of arrangement 614 has no recesses 52 and 76, and is instead rounded in these areas similar to the opposite side of the housing wall 650 adjacent working channel 642. As in arrangement 14, housing wall 650 is split so as to define a slot 670 which extends radially outwardly from, and communicates with, clamp opening 690. In the illustrated embodiment, clamp opening 690 is sized so as to be smaller than the outer diameter of a surgical instrument, such as cannula 13. In one embodiment, opening 690 is approximately 0.002-0.005 inches smaller than the outer diameter of cannula 13. It will be appreciated that the working channel member 642, cover 643, and/or seals 751, 752 may be omitted from this embodiment, similar to arrangement 214.

The use of arrangement 614 is similar to arrangement 14 described above, except that the cannula 13 is maintained in the desired position relative to hub assembly 640 solely via a friction-fit of cannula 13 within clamp opening 690. In this regard, when the cannula 13 is inserted into opening 690 of hub assembly 640, the clamping walls 668 and 669 deflect away from one another so as to slightly widen both clamp opening 690 and slot 670. The pretension of clamping walls 668 and 669 (provided via the semi-elastic nature of the plastic material from which hub 641 is constructed) and the undersizing of clamp opening 690 as mentioned above maintains the cannula 13 in the desired position relative to hub assembly 640.

Figure 34:
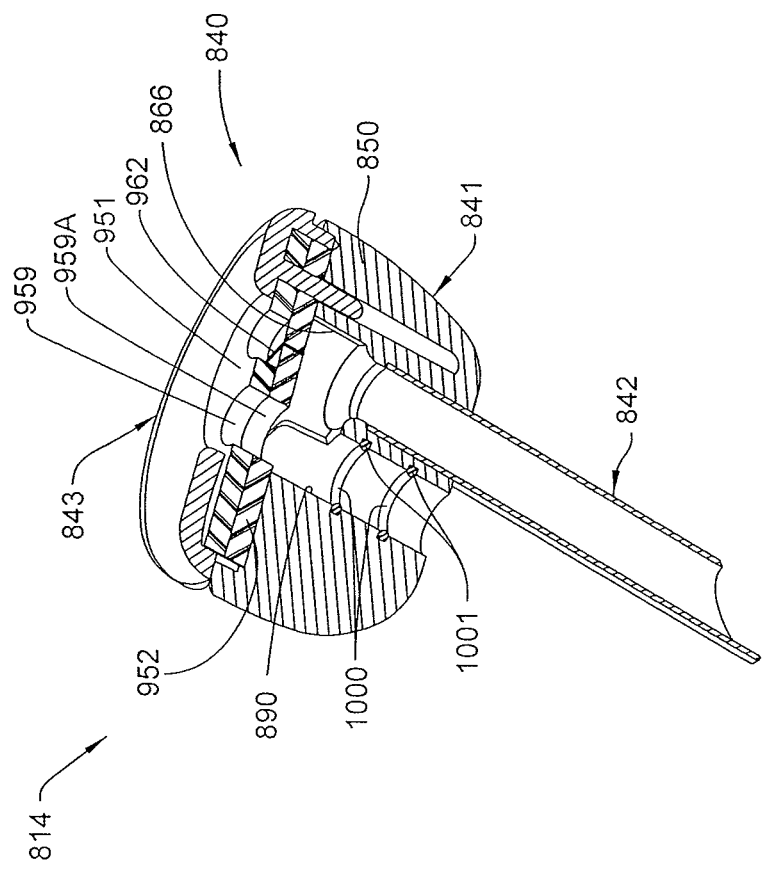
FIG. 34 is a cross-sectional view as seen generally along line 34-34 in FIG. 33.
Figure 33:
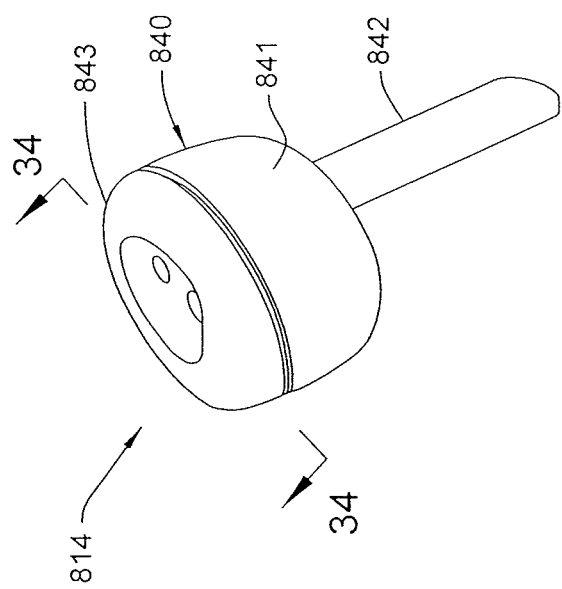
FIG. 33 is a top and front perspective view of a fourth embodiment of the access and positioning arrangement according to the invention.

An additional or fourth embodiment of the access and positioning arrangement is illustrated in FIGS. 33 and 34. Components of access and positioning arrangement 814 which are similar or identical to components of arrangement 14 are provided with the same reference numbers, plus 800. Arrangement 814 includes a hub assembly 840, a working channel 842 fixed to hub 841 of hub assembly 840, and a cover 843 which closes off the upper end of hub 841. In this embodiment, no locking arrangement 45 is provided, housing wall 850 of hub 841 is not recessed (as is housing wall 50 at 52 and 76) and is not split or slotted (as is housing wall 50 at 70), and instead housing wall 850 is continuously rounded and closed on the side there of opposite channel member 842. Similarly, cover or lid 843 is not slotted as in prior embodiments, and instead is closed. As best shown in FIG. 34, housing wall 850 of hub 841 defines a pair of annular and vertically-spaced channels 1000 which open inwardly and into clamp opening 890, and extend radially outwardly away from clamp opening 890 and into housing wall 850. These channels 1000 define respective seats for O-rings 1001 which project slightly radially inwardly and into clamp opening 890. It will be appreciated that the working channel member 842, cover 843, and/or seals 951, 952 may be omitted from this embodiment, similar to arrangement 214.

The use of arrangement 814 is similar to arrangement 14, except that the surgical instrument or cannula 13 is maintained in the desired position relative to hub assembly 840 solely via a friction-fit of cannula 13 within clamp opening 890. In this regard, when cannula 13 is inserted downwardly into opening 890 of hub assembly 840 and through O-rings 1001, O-rings 1001 effectively grip the outer surface of cannula 13 and maintain the position of same relative to hub assembly 840 via a friction-fit.

It will be appreciated that the access and positioning arrangement 814 may omit O-rings 1001 and instead may be constructed so that hub 841 is constructed of an elastomeric material, such as rubber. In this embodiment channel 890 defined in the elastomeric hub 84 has a diameter which is slightly less than the outer diameter of the surgical instrument, i.e. the cannula 13, such that the cannula 13 can be inserted into and through the channel 890 and maintained therein solely through the compressive force of the elastomeric material of the hub 841. The opposite channel is accordingly sized to be greater than the outer diameter of the surgical instrument to be inserted therein, so as to allow the user to freely manipulate the surgical instrument. It will be appreciated that the working channel member, cover, and/or seals may be omitted from this embodiment, similar to arrangement 214.

It will be appreciated that channel member 42, 642, 842 in the illustrated embodiments is constructed of rigid metal, such as stainless steel. However, the channel member can instead be constructed of a flexible material. Such a construction would allow the user to utilize the arrangements 14, 614, 814 with surgical instruments having multiple bends or complex curvatures, such as surgical instrument 212 described above. It will be appreciated that this embodiment would require more effort and/or skill on the part of the user in placing the surgical instrument located within the flexible channel member within the field of view of the endoscope 15. However, the flexible channel member would help to maintain a path or conduit into the surgical site open to prevent tissue from getting in the way of the surgical instrument. Additionally, the flexible channel member can be constructed of a transparent material, which would make the surgical instrument located therein more visible.

Although particular preferred embodiments of the invention have been disclosed in detail for illustrative purposes, it will be recognized that variations or modifications of the disclosed apparatus, including the rearrangement of parts, lie within the scope of the present invention.

What is claimed is:

1. An access and positioning arrangement for use in an endoscopic surgical procedure in which first and second surgical instruments are utilized, said arrangement comprising:
   a housing configured for positioning adjacent a surgical portal defined in a patient, said housing defining therein a first channel configured for receiving a first surgical instrument and a second channel configured for receiving a second surgical instrument, said second channel being disposed in sidewardly-spaced relation from said first channel;
   a clamping arrangement including a clamping member mounted on said housing and disposed adjacent said first channel, and a locking arm mounted on said housing adjacent said clamping member, said locking arm and said clamping member defining respective cooperating cam surfaces, said locking arm being movably mounted to said housing and movable relative to said housing into a locked position, said cam surfaces in said locked position of said locking arm being disposed relative to one another to deflect said clamping member into a clamping position relative to said first channel to non-movably fix the first surgical instrument within said first channel and relative to said housing, and said locking arm being movable relative to said housing into an unlocked position, said cam surfaces in said unlocked position of said locking arm being disposed relative to one another to position said clamping member in an unclamped position allowing movement of the first surgical instrument within said first channel and relative to said housing; and
   a sealing member integral with said housing and sealing upper ends of said first and second channels by sealingly engaging around the first and second surgical instruments when located within the respective said first and second channels.

2. The arrangement of claim 1, wherein said housing includes a wall structure and said clamping member forms part of said wall structure and defines part of said first channel, said first channel having an axis and a first dimension oriented transversely to the axis in said unclamped position of said clamping member and a second dimension oriented transversely to the axis in said clamped position of said clamping member, said second dimension being less than said first dimension.

3. The arrangement of claim 2, wherein said clamping member is a first clamping member and said part of said first channel is a first part, said wall structure including a second clamping member disposed in opposed but spaced-apart relation with said first clamping member and defining a second part of said first channel disposed in opposed but spaced-apart relation with said first part, said locking arm being rotatably mounted to said first and second clamping members.

4. The arrangement of claim 2, wherein said first and second channels open downwardly through a bottom wall of said housing for communication with the surgical portal, said second channel has a generally centrally-located longitudinal axis and said arrangement includes an elongate tubular member cantilevered from said bottom wall in axially aligned relation with said second channel and non-movably fixed to said housing in a predefined and fixed axial position relative thereto, said tubular member having a hollow interior in communication with said second channel, and said second channel and said tubular member together defining a hollow working channel for receiving the second surgical instrument.

5. The arrangement of claim 4, wherein the axes of said first and working channels are oriented in sidewardly-spaced relation with one another so as to maintain the first and second surgical instruments when located within said first and working channels in fixed and sidewardly-spaced relation with one another.

6. The arrangement of claim 5, wherein said tubular member is linear, and the axes of said first and working channels are oriented in non-parallel relationship with one another such that said tubular member angles toward the first surgical instrument, when located within said first channel, as said tubular member projects away from said housing.

7. The arrangement of claim 1, wherein said housing defines therein a generally hollow interior, said first and second channels being disposed within said interior of said housing and opening upwardly through an upper area of said housing and downwardly through a lower area of said housing for communication with a surgical site defined within the patient and accessible through the surgical portal, said sealing member being located within said interior of said housing and disposed to seal said interior and the surgical site to prevent escape of fluids from said housing and to maintain a predefined pressure at the surgical site.

8. The arrangement of claim 7, wherein said sealing member defines therein first and second openings disposed in aligned relation with the respective said first and second channels, said first and second channels each having an axis and respective dimensions oriented transversely relative to the respective axis, said first opening having a dimension less than the dimension of said first channel and said second opening having a dimension less than the dimension of said second channel.

9. The arrangement of claim 7, wherein said housing has an upper peripheral edge portion through which said upper area of said housing opens, said arrangement further including a cover disposed on said upper edge portion, said sealing member being sandwiched between said cover and said housing.

10. The arrangement of claim 1, wherein said first channel is sized for receiving an endoscopic imaging device and said second channel is sized for receiving a surgical instrument for manipulating tissue at a surgical site accessible through the surgical portal, said second channel being disposed in sidewardly-spaced and fixed relation with said first channel.

11. An access and positioning arrangement for use in an endoscopic surgical procedure in which first and second surgical instruments are utilized in conjunction with one another, said arrangement comprising:

a housing configured for positioning adjacent a surgical portal defined in a patient and defining therein a first channel configured for receiving a first surgical instrument and a second channel configured for receiving a second surgical instrument and disposed in sidewardly-spaced relation with said first channel, said first and second channels being disposed within an interior of said housing and opening upwardly through an upper area of said housing and downwardly through a lower area of said housing for communication with a surgical site defined within the patient and accessible through the surgical portal;

a sealing member located within said interior of said housing and disposed to seal said interior of said housing and the surgical site from an environment located exteriorly of the surgical site; and a clamping arrangement provided on said housing and including an actuator member disposed to cooperate with said first channel to non-movably fix the first surgical instrument within said first channel and relative to said housing.

12. The arrangement of claim 11, wherein said first and second channels open downwardly through a bottom wall of said housing for communication with the surgical portal, and said arrangement includes an elongate tubular member cantilevered from said bottom wall in aligned relation with said second channel and having an interior in communication therewith, said second channel and said tubular member together defining a hollow working channel for receiving the second surgical instrument, said tubular member being an integral component of said housing and being non-movably fixed thereto in a predefined and fixed axial position.

13. The arrangement of claim 11, wherein said sealing member defines therein first and second openings disposed in aligned relation with the respective said first and second channels, said first and second channels each having an axis and respective dimensions oriented transversely relative to the respective axes, said first opening having a dimension less than the dimension of said first channel and said second opening having a dimension less than the dimension of said second channel so that the sealing member sealingly engages around the first and second surgical instruments when located within the respective said first and second channels.

14. The arrangement of claim 11, wherein said housing has an upper peripheral edge portion through which said upper area of said housing opens, said arrangement further including a cover disposed on said upper edge portion, and said sealing member being compressed between said cover and said housing.

15. The arrangement of claim 11, wherein said clamping arrangement includes a clamping member mounted on said housing adjacent said first channel, said actuator member and said clamping member defining respective cooperating cam surfaces, said actuator member being mounted to said housing and movable relative to said housing into a locked position, said cam surfaces in said locked position of said actuator member being disposed relative to one another to deflect said clamping member into a clamping position relative to said first channel to non-movably fix the first surgical instrument within said first channel and relative to said housing, and said actuator member being movable relative to said housing into an unlocked position, said cam surfaces in said unlocked position of said actuator member being disposed relative to one another to position said clamping member in an unclamped position allowing movement of the first surgical instrument within said first channel and relative to said housing.

16. The arrangement of claim 15, wherein said housing includes a wall structure and said clamping member forms part of said wall structure and defines part of said first channel, said first channel having an axis and a first dimension oriented transversely to the axis in said unclamped position of said clamping member and a second dimension oriented transversely to the axis in said clamped position of said clamping member, said second dimension being less than said first dimension.

17. The arrangement of claim 16, wherein said clamping member is a first clamping member and said part of said first channel is a first part, said wall structure including a second clamping member disposed in opposed but spaced-apart relation with said first clamping member and defining a second part of said first channel disposed in opposed but spaced-apart relation with said first part, said actuator member being rotatably mounted to said first and second clamping members.

18. The arrangement of claim 11, wherein said sealing member is a first sealing member and said arrangement includes a second sealing member disposed in superimposed relation with said first sealing member within said upper area in said interior of said housing.

19. An access and positioning arrangement for use in an endoscopic surgical procedure in which first and second surgical instruments are utilized in conjunction with one another, said arrangement comprising a housing configured for positioning adjacent a surgical portal defined in a patient and defining therein a first channel configured for receiving a first surgical instrument and a second channel configured for receiving a second surgical instrument and disposed in sidewardly-spaced relation with said first channel, said first and second channels being disposed within an interior of said housing and opening upwardly through an upper area of said housing and downwardly through a lower area of said housing for communication with a surgical site defined within the patient and accessible through the surgical portal, said housing defining a clamping arrangement disposed adjacent said first channel, said clamping arrangement including first and second clamping members forming part of said housing and disposed in opposed but spaced-apart relation with one another to define a slot therebetween which extends through said housing and communicates with said first channel, said first and second clamping members and said first channel being constructed of a resilient material such that said first and second clamping members deflect away from one another and enlarge said first channel when the first surgical instrument is inserted therein and automatically compressively engage, along with said first channel, the first surgical instrument to maintain same in a desired position relative to said housing solely via friction without the need for any presetting or tightening action of said clamping arrangement by a user prior to or after insertion of the first surgical instrument into said first channel.

20. The arrangement of claim 19, wherein said arrangement further includes an elongate tubular member cantilevered from a bottom of said housing in aligned relation with said second channel and having a hollow interior in communication therewith, said tubular member being fixed in a non-removable manner to said housing in a predefined and permanent position relative thereto, said second channel and said tubular member together defining a hollow working channel for receiving the second surgical instrument.

21. The arrangement of claim 19, wherein said first and second channels have respective upper ends which open upwardly through said upper area of said housing and respective lower ends which open downwardly through said lower area of said housing for communication with the surgical site, said upper ends of said first and second channel being sized to receive the respective first and second surgical instruments therein through said upper area of said housing.

22. An access and positioning arrangement for use in an endoscopic surgical procedure in which first and second surgical instruments are utilized, said arrangement comprising:
a housing configured for positioning adjacent a surgical portal defined in a patient, said housing defining therein a first channel configured for receiving a first surgical instrument and a second channel configured for receiving a second surgical instrument, said second channel being disposed in sidewardly-spaced relation from said first channel and opening downwardly through a bottom wall of said housing for communication with the surgical portal;
a clamping arrangement provided on said housing and disposed to cooperate with said first channel to non-movably fix the first surgical instrument within said first channel and relative to said housing; and
an elongate tubular member cantilevered from said bottom wall in aligned relation with said second channel and having a hollow interior in communication therewith, said tubular member being non-movably fixed to said housing in a pre-defined and fixed axial position relative thereto, said second channel and said tubular member together defining a hollow working channel for receiving the second surgical instrument.

23. The arrangement of claim 22, wherein said first channel and said working channel have respective generally centrally-located longitudinal axes oriented in sidewardly-spaced relation with one another so as to maintain the first and second surgical instruments in sidewardly-spaced relation with one another when located within the respective said first and working channels, the axes of said first and working channels being oriented in non-parallel relationship with one another such that said tubular member angles toward the first surgical instrument, when same is located within said first channel, as said tubular member projects away from said bottom wall of said housing, said tubular member having a chamfered terminal end spaced from said bottom wall of said housing, and said tubular member is both axially and rotationally non-movably fixed to said housing with an acute portion of said chamfered terminal end being located closer to the axis of said first channel than a remaining portion of said chamfered terminal end.

24. An access and positioning arrangement for use in an endoscopic surgical procedure in which first and second surgical instruments are utilized in conjunction with one another, said arrangement comprising a housing configured for positioning adjacent a surgical portal defined in a patient and defining therein a first channel configured for receiving a first surgical instrument and a second channel configured for receiving a second surgical instrument and disposed in sidewardly-spaced relation with said first channel, said first and second channels being disposed within an interior of said housing and having upper ends which open upwardly through an upper area of said housing and lower ends which open downwardly through a lower area of said housing for communication with a surgical site defined within the patient and accessible through the surgical portal, said upper ends of said first and second channels being sized to receive the respective first and second surgical instruments therein through said upper area of said housing, each said first and second channel having a substantially constant diameter along a length thereof between the respective said upper and lower ends thereof, said housing including an elastomeric region located within said first channel and defining a portion thereof, said elastomeric region being sized to frictionally engage an exterior of the first surgical instrument when same is inserted into said first channel so as to automatically compressively engage the first surgical instrument and maintain same in a desired position relative to said housing solely via friction when the first surgical instrument is inserted into said first channel.

25. The arrangement of claim 24, wherein said elastomeric region comprises an annular elastomeric member disposed within said first channel within said housing.

* * * * *